US012733814B2

(12) United States Patent
Moehring et al.

(10) Patent No.: US 12,733,814 B2
(45) Date of Patent: Sep. 15, 2026

(54) INFRARED OTOSCOPE FOR CHARACTERIZATION OF EFFUSION

(71) Applicant: OtoNexus Medical Technologies, Inc., Seattle, WA (US)

(72) Inventors: Mark A. Moehring, Seattle, WA (US); George A. Gates, Boerne, TX (US); Daniel Kreindler, Foster City, CA (US); Jay A. Chesavage, Palo Alto, CA (US)

(73) Assignee: OtoNexus Medical Technologies, Inc., Seattle, WA (US)

( * ) Notice: Subject to any disclaimer, the term of this patent is extended or adjusted under 35 U.S.C. 154(b) by 824 days.

(21) Appl. No.: 17/714,643

(22) Filed: Apr. 6, 2022

(65) Prior Publication Data

US 2022/0225881 A1 Jul. 21, 2022

Related U.S. Application Data

(63) Continuation-in-part of application No. 16/438,603, filed on Jun. 12, 2019, now Pat. No. 11,317,811,
(Continued)

(51) Int. Cl.
*H04B 10/00* (2013.01)
*A61B 1/00* (2006.01)
(Continued)

(52) U.S. Cl.
CPC ........ *A61B 5/0086* (2013.01); *A61B 1/00009* (2013.01); *A61B 1/00165* (2013.01);
(Continued)

(58) Field of Classification Search
CPC .............. A61B 5/0086; A61B 1/00009; A61B 1/00165; A61B 1/0638; A61B 1/0669;
(Continued)

(56) References Cited

U.S. PATENT DOCUMENTS

| | | |
|---|---|---|
| 5,115,133 A | 5/1992 | Knudson et al. |
| 5,321,501 A | 6/1994 | Swanson et al. |

(Continued)

FOREIGN PATENT DOCUMENTS

| | | |
|---|---|---|
| EP | 3182886 A4 | 5/2018 |
| EP | 3641634 A4 | 3/2021 |

(Continued)

OTHER PUBLICATIONS

Burkhardt et al. Investigation of the human tympanic membrane oscillation ex vivo by Doppler optical coherence tomography. J. Biophotonics 7, No. 6, 434-441 (2014).

(Continued)

*Primary Examiner* — Agustin Bello
(74) *Attorney, Agent, or Firm* — Wilson Sonsini Goodrich & Rosati

(57) ABSTRACT

An otoscope uses differential reflected response of optical energy at an absorption range and an adjacent wavelength range to determine the presence of water (where the wavelengths are water absorption wavelength and adjacent non-absorption excitation wavelengths). In another example of the invention, the otoscope utilizes OCT in combination with absorption and non-absorption range for bacteria and water.

32 Claims, 12 Drawing Sheets

Related U.S. Application Data which is a continuation of application No. 15/609,015, filed on May 31, 2017, now Pat. No. 10,357,161, application No. 17/714,643 is a continuation-in-part of application No. 16/043,584, filed on Jul. 24, 2018, now Pat. No. 11,602,275, which is a continuation of application No. 15/188,750, filed on Jun. 21, 2016, now Pat. No. 10,568,515.

(51) Int. Cl.

| | |
|---|---|
| ***A61B 1/06*** | (2006.01) |
| ***A61B 1/227*** | (2006.01) |
| ***A61B 5/00*** | (2006.01) |
| ***A61B 5/12*** | (2006.01) |
| ***A61B 5/145*** | (2006.01) |
| ***A61B 8/00*** | (2006.01) |
| ***G01B 9/02091*** | (2022.01) |
| *A61B 1/07* | (2006.01) |
| *G01J 5/02* | (2022.01) |
| *G01J 5/04* | (2006.01) |
| *G02B 6/036* | (2006.01) |
| *G02B 23/24* | (2006.01) |

(52) U.S. Cl.

CPC .......... *A61B 1/0638* (2013.01); *A61B 1/0669* (2013.01); *A61B 1/227* (2013.01); *A61B 5/0066* (2013.01); *A61B 5/12* (2013.01); *A61B 5/14507* (2013.01); *A61B 8/44* (2013.01); *G01B 9/02091* (2013.01); *A61B 1/0646* (2013.01); *A61B 1/07* (2013.01); *G01J 5/02* (2013.01); *G01J 5/04* (2013.01); *G02B 6/03694* (2013.01); *G02B 23/24* (2013.01)

(58) Field of Classification Search

CPC ......... A61B 1/227; A61B 5/0066; A61B 5/12; A61B 5/14507; A61B 8/44; A61B 1/0646; A61B 1/07; A61B 5/6817; G01B 9/02091; G01J 5/02; G01J 5/04; G01J 3/0218; G01J 3/0256; G01J 3/42; G01J 3/4531; G01J 3/4535; G01J 3/457; G02B 6/03694; G02B 23/24; G02B 23/2423; G02B 23/2484

See application file for complete search history.

(56) References Cited

U.S. PATENT DOCUMENTS

| | | | | |
|---|---|---|---|---|
| 5,383,467 | A | 1/1995 | Auer et al. | |
| 6,950,692 | B2 | 9/2005 | Gelikonov et al. | |
| 7,632,232 | B2 | 12/2009 | Lewandowski et al. | |
| 7,751,057 | B2 | 7/2010 | Oldenburg et al. | |
| 8,115,934 | B2 * | 2/2012 | Boppart | A61B 5/0066 356/497 |
| 8,594,757 | B2 | 11/2013 | Boppart et al. | |
| 9,014,792 | B2 | 4/2015 | Goldfain et al. | |
| 9,364,148 | B2 | 6/2016 | Roberts | |
| 9,638,511 | B2 | 5/2017 | Boppart et al. | |
| 9,788,712 | B2 | 10/2017 | Seth et al. | |
| 9,867,528 | B1 * | 1/2018 | Boppart | A61B 5/0053 |
| 9,918,622 | B2 | 3/2018 | Seth et al. | |
| 10,258,238 | B2 | 4/2019 | Boppart et al. | |
| 10,278,570 | B2 | 5/2019 | Shelton et al. | |
| 10,296,780 | B2 | 5/2019 | Karygianni et al. | |
| 10,327,627 | B2 | 6/2019 | Berkner et al. | |
| 10,357,161 | B1 | 7/2019 | Chesavage et al. | |
| 10,401,141 | B2 | 9/2019 | Boppart et al. | |
| 10,568,515 | B2 * | 2/2020 | Moehring | A61B 5/7278 |
| 10,660,604 | B2 | 5/2020 | Moehring et al. | |
| 10,709,365 | B2 | 7/2020 | Cohen et al. | |
| 10,772,541 | B2 | 9/2020 | Klein et al. | |
| 11,317,811 | B2 | 5/2022 | Moehring et al. | |
| 11,602,275 | B2 * | 3/2023 | Moehring | A61B 5/6817 |
| 2002/0087084 | A1 | 7/2002 | Shahar et al. | |
| 2003/0171655 | A1 | 9/2003 | Newman et al. | |
| 2005/0059868 | A1 | 3/2005 | Schurman | |
| 2006/0229509 | A1 | 10/2006 | Al-Ali et al. | |
| 2006/0282009 | A1 | 12/2006 | Oberg et al. | |
| 2007/0112273 | A1 * | 5/2007 | Rogers | G01N 21/359 600/475 |
| 2007/0129632 | A1 | 6/2007 | Voie et al. | |
| 2009/0037922 | A1 | 2/2009 | Herington | |
| 2009/0185191 | A1 | 7/2009 | Boppart et al. | |
| 2011/0286505 | A1 | 11/2011 | Hedley et al. | |
| 2013/0023914 | A1 | 1/2013 | Truong et al. | |
| 2013/0060131 | A1 * | 3/2013 | Oghalai | A61B 1/00165 600/425 |
| 2013/0165763 | A1 | 6/2013 | Huang et al. | |
| 2013/0289353 | A1 | 10/2013 | Seth et al. | |
| 2013/0342826 | A1 | 12/2013 | Goldfain et al. | |
| 2014/0206979 | A1 | 7/2014 | Berkner et al. | |
| 2014/0249426 | A1 | 9/2014 | Huh et al. | |
| 2014/0316278 | A1 | 10/2014 | Addison et al. | |
| 2015/0148654 | A1 | 5/2015 | Whanwook et al. | |
| 2015/0169435 | A1 | 6/2015 | Wu et al. | |
| 2015/0374208 | A1 | 12/2015 | Ruppersberg et al. | |
| 2016/0007840 | A1 * | 1/2016 | Boppart | A61B 5/6817 600/188 |
| 2016/0040978 | A1 * | 2/2016 | Boppart | G01B 9/02091 356/479 |
| 2017/0049309 | A1 | 2/2017 | Lepple-Wienhues | |
| 2018/0242847 | A1 | 8/2018 | Boppart et al. | |
| 2018/0256031 | A1 | 9/2018 | Adamson et al. | |
| 2018/0303348 | A1 | 10/2018 | Boppart et al. | |
| 2018/0353079 | A1 | 12/2018 | Chesavage et al. | |
| 2019/0142258 | A1 | 5/2019 | Shelton et al. | |
| 2019/0320887 | A1 | 10/2019 | Shelton et al. | |
| 2019/0343390 | A1 | 11/2019 | Boppart et al. | |
| 2019/0368929 | A1 * | 12/2019 | Zhang | G01J 3/0275 |
| 2022/0225881 | A1 * | 7/2022 | Moehring | G01J 3/0218 |

FOREIGN PATENT DOCUMENTS

| | | | |
|---|---|---|---|
| JP | S55500123 | A | 3/1980 |
| JP | S59500455 | A | 3/1984 |
| JP | 2007500542 | A | 1/2007 |
| JP | 2008531215 | A | 8/2008 |
| JP | 2014519393 | A | 8/2014 |
| WO | WO-2013160780 | A4 | 1/2014 |
| WO | WO-2015169435 | A1 | 11/2015 |
| WO | WO-2016182999 | A1 | 11/2016 |
| WO | WO-2017222947 | A1 | 12/2017 |
| WO | WO-2018129430 | A1 | 7/2018 |
| WO | WO-2018160561 | A1 | 9/2018 |
| WO | WO-2018222782 | A1 | 12/2018 |

OTHER PUBLICATIONS

Chang et al. Simultaneous 3D imaging of sound-induced motions of the tympanic membrane and middle ear ossicles. Hearing Research 304 (2013) 49-56.

EP20170815982.8 Summons to Attend Oral Proceedings dated Jan. 30, 2024.

U.S. Appl. No. 16/043,584 Notice of Allowance dated Nov. 9, 2022.

EP17815982.8 Extended Search Report dated Jan. 8, 2020.

EP18808827.2 European Search Report dated Sep. 29, 2020.

International search report with written opinion dated Aug. 7, 2018 for PCT/US2018/035228.

International search report with written opinion dated Oct. 24, 2017 for PCT/US2017/038052.

U.S. Appl. No. 15/188,750 Notice of Allowance dated Nov. 13, 2019.

Office action dated Mar. 7, 2019 for U.S. Appl. No. 15/188,750.

Sorrell et al., Bacteria Identification of Otitis Media with Fluorescence Spectroscopy, Lasers in Surgery and Medicine, 14:155-163 (1994).

(56) References Cited

OTHER PUBLICATIONS

Spector et al., Noninvasive Fluorescent Identification of Bacteria Causing Acute Otitis Media in a Chinchilla Model, The Laryngoscope, 110:1119-1123 (2000).
U.S. Appl. No. 15/609,015 Notice of Allowance dated Mar. 14, 2019.
U.S. Appl. No. 15/188,750 Office Action dated Mar. 7, 2019.
U.S. Appl. No. 15/609,015 Office Action dated Jul. 6, 2018.
U.S. Appl. No. 16/043,584 Office Action dated Dec. 18, 2020.
U.S. Appl. No. 16/043,584 Office Action dated Jul. 14, 2021.
U.S. Appl. No. 16/043,584 Office Action dated Mar. 16, 2021.
U.S. Appl. No. 16/043,584 Office Action dated Nov. 23, 2021.
U.S. Appl. No. 16/043,584 Office Action dated Sep. 18, 2020.
U.S. Appl. No. 16/438,603 Notice of Allowance dated Jan. 7, 2022.
U.S. Appl. No. 16/438,603 Office Action dated Mar. 30, 2021.

* cited by examiner

IR Spectroscopy system

IR Speculum Tip detail

Normalized spectral response from TM

Measurement waveforms

FIG. 5

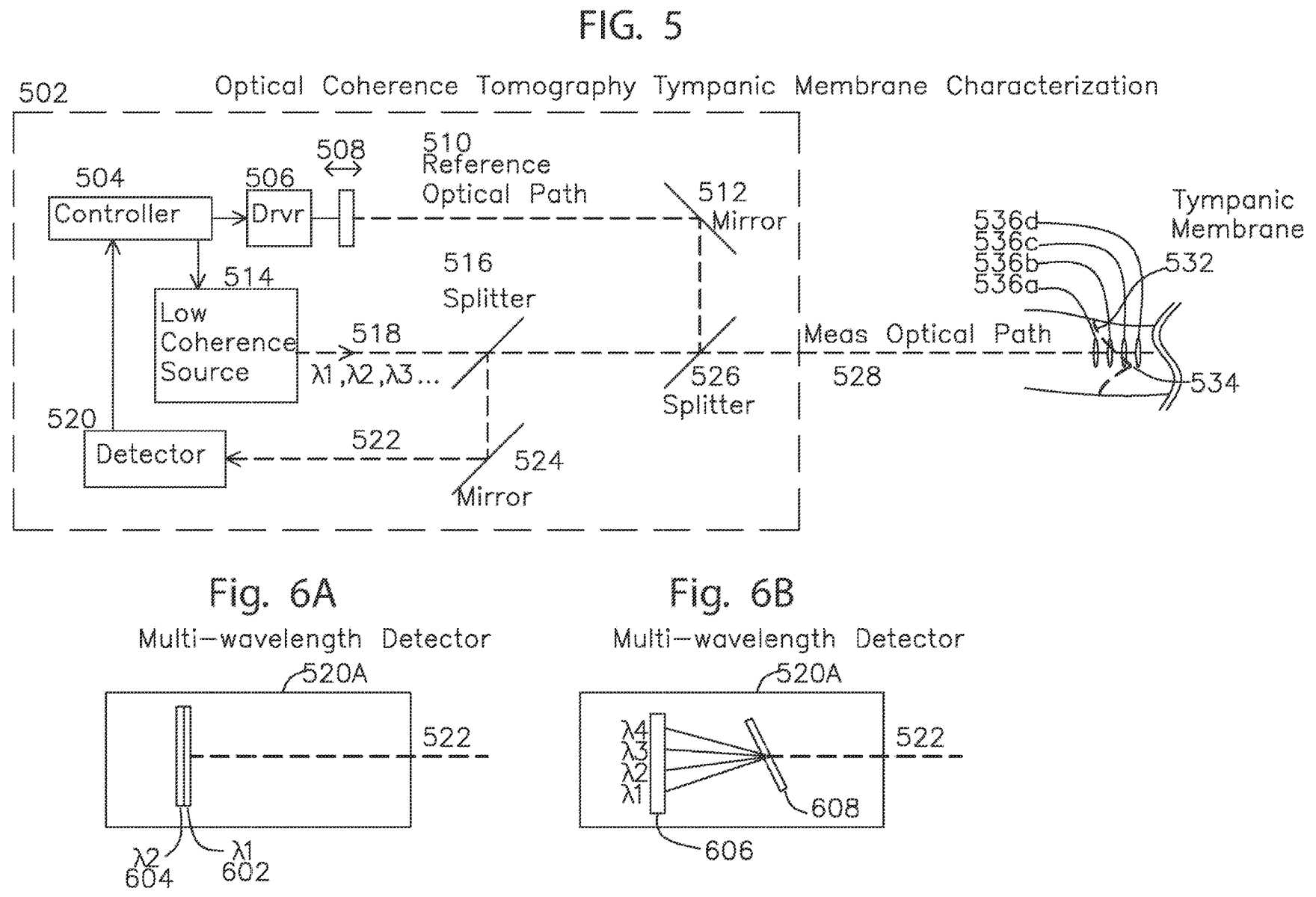

Optical Coherence Tomography Tympanic Membrane Characterization 502
504 Controller
506 Drvr
508
510 Reference Optical Path
512 Mirror
514 Low Coherence Source
516 Splitter
518 λ1,λ2,λ3...
520 Detector
522
524 Mirror
526 Splitter
528 Meas Optical Path
Tympanic Membrane
532
534
536a
536b
536c
536d

Fig. 6A

Multi-wavelength Detector
520A
522
λ1 602
λ2 604

Fig. 6B

Multi-wavelength Detector
520A
522
608
606
λ4 λ3 λ2 λ1

No Effusion (λ1,λ2)

No Effusion (λ3,λ4)

Increase Ref length
Decrease Ref length
0
−0.5
+0.5
+1
0
+0.5
0
−1
+0.5
+1
0
+0.5
701
703
λ1
702
706
708
712
710
714
λ2
740
744
748
713
746
750
λ3
703
718
721
722
720
724
λ4
741
754
757
758
760
756

Viral Effusion
(λ1,λ2)
Increase Ref length
Decrease Ref length
801
+1
0
−0.5
+0.5
0
+0.5

808
814
812
λ1
802
806
810

848
850
841
λ2
840
844
846

Viral Effusion
(λ3,λ4)
803
0
−1
+0.5
+1
0
+0.5

856
824
822
λ3
803
818
820

856
858
λ4
841
854
860

Bacterial Effusion (λ1,λ2)

Bacterial Effusion (λ3,λ4)
Increase Ref length
Decrease Ref length
901
903
0
−0.5
+0.5
+1
0
+0.5
0
−1
+0.5
+1
0
+0.5

908
950
914
912
956
924
922
λ1
902
906
λ3
903
918
910
920

948
950
947
956
958
λ2
940
944
λ4
941
954
946
960

Optical Waveguide system for OCT measurement of TM
1000
1001
Cntrlr
1002
Low Coherence Source
Detector
1022
1016
1004
λ1..λ4
1020
Splitter 1
1006
1008
Splitter 2
1010
1017
1019
PZT modulator
1014
1012
Lref
1013
1015
Lmeas
1021d
1021c
1021b
1021a
1050
1051

Optical Coherence Tomography Tympanic Membrane Characterization
1100
1102
Low Coherence Source
1124
Detector
1104
1122
1106
Splitter
1104
Mirror
1108
Splitter
1110
Mirror
Meas Optical Path
1118
1112
Reference Optical Path
1114
1126d
1126c
1126b
1126a
Tympanic Membrane
1115
1119
1116
Mech Drvr
1117
Controller Mech Drvr
axial displacement
actuator voltage Mech Drvr
displacement
1202d
1202c
1202b
1202a
time
T1
T2
T3
T4
T5
T6
T7

Temporal TM positional sensing system Ref Drive
Increase Ref length
Decrease Ref length
1502
0
−0.5
−1
−0.5
0
+0.5
0
−1
−2
−1
0
+1

Detector Signal
1506
1507
1508
1504
1509
1520
1522
1511

Optical Waveguide system for OCT measurement of TM
1600
1618
Cntrlr
1602
Low Coherence Source
Detector
1622
1616
1604
1620
Splitter 1
1606
1608
Splitter 2
1610
1617
1612
Lref
1613
PZT modulator
1614
1619
1615
Lmeas
1621d
1621c
1621b
1621a
1650
1651

FIG. 17

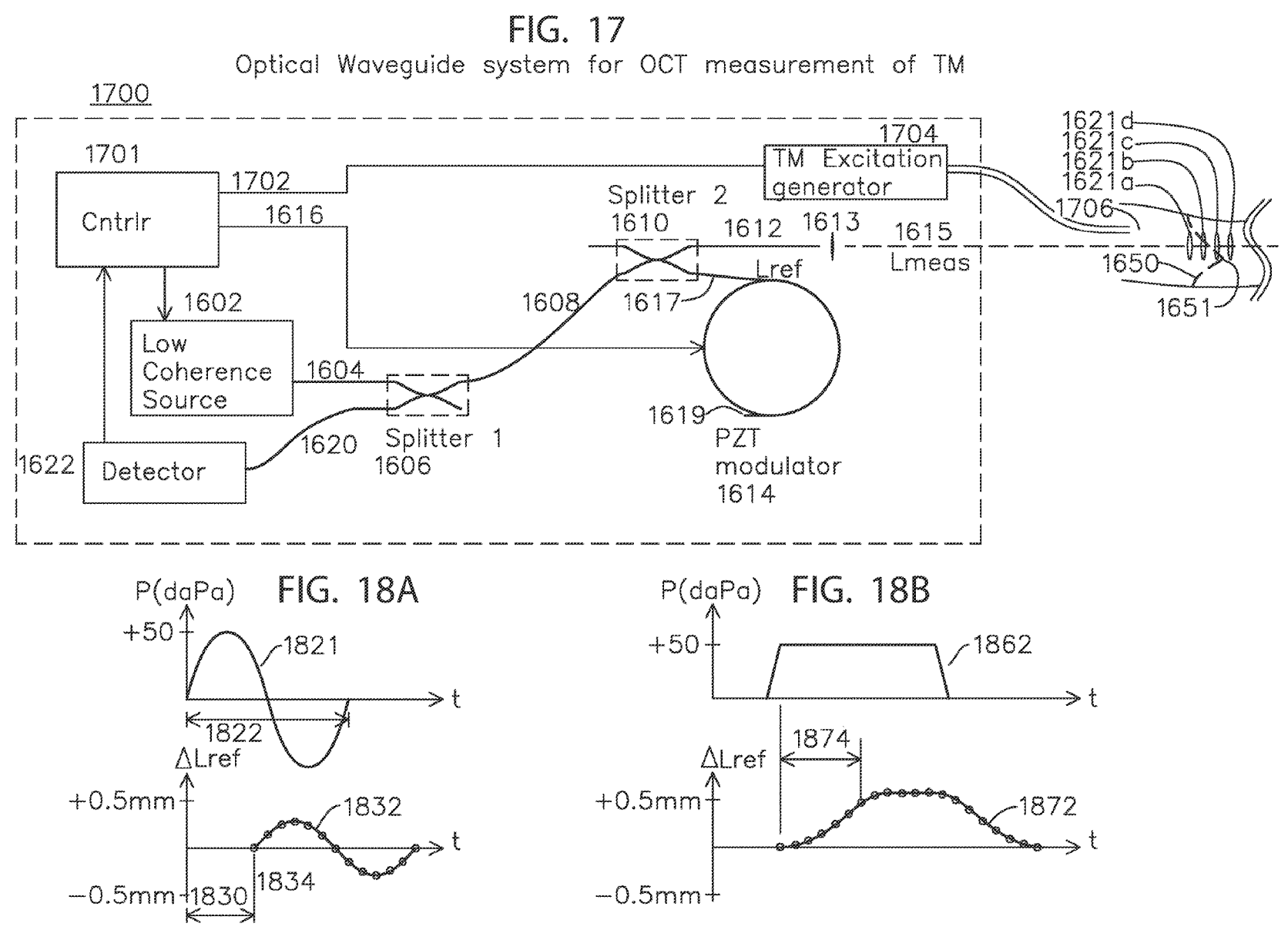

Optical Waveguide system for OCT measurement of TM

1700

1701 Cntrlr

1702

1616

1602 Low Coherence Source

1622 Detector

1604

1620

Splitter 1 1606

1608

Splitter 2 1610

1617

1619

PZT modulator 1614

1612 Lref

1613

1615 Lmeas

1704 TM Excitation generator

P(daPa)

+50

1821

1822 t

ΔLref

P(daPa)

+50

1862 t

ΔLref

+0.5mm

−0.5mm

1874

1872 t

INFRARED OTOSCOPE FOR CHARACTERIZATION OF EFFUSION

CROSS-REFERENCE

This is a continuation-in-part of U.S. application Ser. No. 16/438,603, filed Jun. 12, 2019, which is a continuation of U.S. application Ser. No. 15/609,015, filed May 31, 2017, now U.S. Pat. No. 10,357,161, issued Jul. 23, 2019, the full disclosures of which are incorporated herein by reference in their entirety; this application is also a continuation-in-part of U.S. application Ser. No. 16/043,584, filed Jul. 24, 2018, which is a continuation of U.S. application Ser. No. 15/188,750, filed Jun. 21, 2016, now U.S. Pat. No. 10,568,515, issued Feb. 25, 2020, the full disclosures of which are incorporated herein by reference in their entirety.

BACKGROUND

Acute Otitis Media (AOM) is a common disease of the inner ear, involving tissue inflammation and fluidic pressure which impinges on the tympanic membrane. Acute Otitis Media may be caused by a viral infection, which generally resolves without treatment, or it may be caused by a bacterial infection, which may progress and cause hearing loss or other deleterious and irreversible effects. Unfortunately, it is difficult to distinguish between viral or bacterial infection using currently available diagnostic devices, and the treatment methods for the two underlying infections are quite different. For bacterial infections, antibiotics are the treatment of choice, whereas for viral infections, the infection tends to self-resolve, and antibiotics are not only ineffective, but may result in an antibiotic resistance which would make them less effective in treating a subsequent bacterial infection. It is important to accurately diagnose acute otitis media, as AOM can be a precursor to chronic otitis media with effusion (COME), for which surgical drainage of the effusion and insertion of a tube in the tympanic membrane is indicated.

The definitive diagnostic tool for inner ear infections is myringotomy, an invasive procedure which involves incisions into the tympanic membrane, withdrawal of fluid, and examination of the effusion fluid under a microscope to identify the infectious agent in the effusion. Because of complications from this procedure, it is only used in severe cases. This presents a dilemma for medical practitioners, as the prescription of antibiotics for a viral infection is believed to be responsible for the evolution of antibiotic resistance in bacteria, which may result in more serious consequences later in life, and with no efficacious treatment outcome, as treatment of viral infectious agents with antibiotics is ineffective. An improved diagnostic tool for the diagnosis of acute otitis media is desired.

SUMMARY

In an aspect, an optical coherence tomography (OCT) device has a low coherence optical source generating optical energy coupled through a first splitter, thereafter to a second splitter, the second splitter having a measurement optical path to a tympanic membrane and also a reference optical path to a reflector which returns the optical energy to the first splitter, where the reflected optical energy is added to the optical energy reflected from the measurement optical path. The combined reflected optical energy is then provided to the first splitter, which directs the optical energy to a detector. The reflector is spatially modulated in displacement along the axis of the reference optical path such that the detector is presented with an optical intensity and optionally a continuum of optical spectral density from a particular measurement path depth, when the measurement optical path and reference optical path are equal in path length. When the device is positioned with the measurement path directed into an ear canal and directing optical energy to a tympanic membrane, by varying the reference optical path length through translation of the location of the reflector along the axis of the reference optical path, a measurement of optical and spectral characteristics of the tympanic membrane may be performed. Additionally, an external pressure excitation may be applied to provide an impulsive or steady state periodic excitation of the tympanic membrane during the OCT measurement, and a peak response and associated time of the peak response identified. The temporal characteristics and positional displacement of the tympanic membrane can be thereafter examined to determine the tympanic membrane response to the external pressure excitation. The evaluation of the tympanic membrane response from the OCT detector data may subsequently be correlated to a particular viscosity or biofilm characteristic. By examination of the temporal characteristic, an estimate of the viscosity of a fluid adjacent to a tympanic membrane may be determined, and the viscosity subsequently correlated to the likelihood of a treatable bacterial infection.

A first object of the invention is a non-invasive medical device for the identification of fluid type adjacent to a tympanic membrane.

A second object of the invention is a method for identification of a fluid adjacent to a tympanic membrane.

A third object of the invention is a method for performing optical coherence tomography for identification of a film characteristic adjacent to a tympanic membrane.

A fourth object of the invention is an apparatus for performing optical coherence tomography for identification of a fluid characteristic adjacent to a tympanic membrane.

An fifth object of the invention is an apparatus and method for characterization of a tympanic membrane and adjacent materials by coupling a pressure excitation source to a tympanic membrane, where the tympanic membrane is illuminated through a measurement path by an optical source having low coherence, the low coherent optical source also coupled to a reference path and to a mirror, where reflections from the mirror and reflections from the tympanic membrane are summed and presented to a detector, the reference path length modulated over a range which includes the tympanic membrane, the detector thereby receiving reflected optical energy from the tympanic membrane through the measurement path and also from the mirror through the reference path, such that modulation of the reference path length at a sufficiently high rate allows for estimation of the tympanic membrane position in response to the pressure excitation, thereby providing characterization of the tympanic membrane and adjacent fluid.

A sixth object of the invention is an optical coherence tomography system having a measurement path and a reference path, the reference path modulated in length, the measurement path and reference path coupled through an optical splitter to an optical source having low coherence, where reflected optical energy from the reference optical path and reflected optical energy from the measurement optical path are summed and provided to a wavelength splitter and thereafter to a plurality of detectors, one detector for each sub-range of wavelengths within the wavelength spectrum of the low coherence optical source, the plurality of detectors coupled to a controller discriminating by wavelength characteristics the detector response for at least two different reflective materials.

In a second aspect, a controller enables one of a first plurality of optical sources, or alternatively a single first optical source at a wavelength for bacterial absorption, and one of a second plurality of optical sources, or alternatively a second optical source operative at an adjacent wavelength which is non-absorptive for bacteria, an optional third source operative at a wavelength absorptive for watery fluid and an optional fourth source operative at an adjacent non-absorptive wavelength for watery fluid, each optical source or sources optionally operative at alternating or exclusive intervals of time. Each wavelength source is optically coupled through a tapered speculum which is inserted into the ear canal of a subject to be examined. The optical beam from each optical source may be carried as a directed beam, or the optical beam may be carried in an annular light guide or light pipe which surrounds the speculum, the optical energy from the illumination configuration impinging onto a front (distal) surface of a tympanic membrane, the tympanic membrane having a bacterial film or bacterial fluid on an opposite (proximal) surface of the tympanic membrane to be characterized. Reflected optical energy is coupled into the speculum tip to a single detector having a first wavelength response for energy reflected from the first source and a second wavelength response for energy reflected from the second wavelength source, or to separate detectors which are operative in each optical wavelength range of a respective optical source. The first wavelength response and second wavelength response are averaged over the associated interval the respective optical source is enabled to form an average measurement for each first wavelength response and each second wavelength response, and a ratio is formed from the two measurements. A first wavelength is in an absorption or scattering range of wavelengths for a bacterium to be characterized, and a second of the wavelengths is adjacent to the first wavelength and outside of the bacterial scattering or absorption wavelength. The response ratio for the first and second wavelength is applied to a polynomial or to a look-up table which provides an estimate of bacterial load from the ratio of power in the first wavelength to the power in the second wavelength, optionally compensating for the wavelength specific attenuation when absorptive or scattering fluid is not present, for example by using a stored wavelength scaling coefficient which compensates for scattering alone. A similar ratio for the detector responses associated with the third and fourth wavelength sources which are in adjacent absorptive and non-absorptive wavelengths, respectively, for water may be formed as well.

In a third aspect providing axial extent specificity over the region of measurement, the first and second wavelength sources are selected as adjacent wavelengths for absorption response and non-absorption response for bacteria, and also have a short coherence length, with the optical output of each source directed to the proximal surface of the tympanic membrane and middle ear to be characterized after splitting the optical energy into a measurement path and a reference path. The measurement path directs optical energy to the fluid to be characterized having a length equal to the reference path, the reflected optical energy from the measured path and reflected path are combined, thereby forming a coherent response over a narrow depth range, which is set to include the proximal surface of the tympanic membrane and middle ear region to be characterized. The first wavelength source and second wavelength source are enabled during exclusive intervals of time, and the combined measurement path and reference path optical energy directed to a detector response to the associated wavelengths. The first wavelength detector response and second wavelength detector response form a ratio which is used as a bacterial load metric, the ratio metric acting as a proxy for detection of the presence of bacteria. The third and fourth wavelengths are selected as in the first example to be adjacent but comparatively scattering and non-scattering for watery fluid, and used to form a second ratio which acts as a proxy for detection of watery fluid in the selected axial extent.

For the second or third aspect, by combining the second metric (presence of watery fluid) with the first metric (presence of bacteria), a more complete survey of the scope of acute otitis media may be determined.

A seventh object of the invention is a device for measurement of infectious agents present in an individual suspected of suffering from acute otitis media, the device having a plurality of optical sources, each optical source operative at a unique wavelength or range of wavelengths, each optical source operative within a particular range of wavelengths for an interval of time which is exclusive from the interval of time when optical sources at other wavelengths are operative, the device having a detector for measurement of reflected optical energy, the detector measuring a ratio of detected optical energy at a first wavelength to detected optical energy at a second or third wavelength, thereafter forming a ratio metric value as a proxy for estimated bacterial load.

An eighth object of the invention is a method for determination of bacterial concentration by successively illuminating a first surface of a membrane using a first and second wavelength at exclusive time intervals, measuring the reflected optical energy from the opposite surface of the membrane during each associated interval, forming a ratio of the first wavelength and second wavelength detector responses from the associated illumination events, each illumination event at a unique wavelength or range of wavelengths, where at least one of the illumination wavelengths corresponds to a bacterial absorption band, and another of the illumination wavelengths is in a wavelength with non-absorption or non-scattering characteristic for a bacterial colony or group of dispersed bacterium.

A ninth object of the invention is a speculum tip for insertion into an ear canal, one or more pairs of optical sources, each optical source coupling an optical output through the speculum tip, each optical source operative in a unique wavelength or range of wavelengths, each pair of optical sources generating a first optical output at a first wavelength selected for reflective attenuation for either watery fluid or bacteria, and also generating a second wavelength selected for comparative non-attenuation reflection for either watery fluid or bacteria, the second wavelength operative near the first wavelength, where reflected optical energy from the tympanic membrane is directed to a detector responsive to each optical source wavelength for optical energy reflected into the speculum tip, the detector coupled to a controller measuring a ratio of detector response from said first and said second wavelength, thereby forming a metric indicating the presence of bacteria and/or watery fluid from the detector response ratio associated with each pair of emitters.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows a block diagram of an OCT measurement system for dual wavelength measurements.

FIG. 6A and FIG. 6B shows a block diagram for a multi-wavelength detector.

FIG. 17 shows an optical waveguide system for measurement of a tympanic membrane with an excitation source.

FIG. 18A shows a plot for a sinusoidal excitation applied to deformable surface or membrane with a reflected response signal.

FIG. 18B shows a plot for a step excitation applied to a deformable surface or membrane, and a response to the step excitation.

DETAILED DESCRIPTION

The present provides an otoscope for characterization of fluid in an ear. The present provides methods, systems, and devices relating to the use of optical coherence tomography (OCT). For example, the OCT may be used in the diagnosis of otitis media (OM). For example, the present disclosure provides methods, systems, and devices related to the detection of bacteria in a fluid opposite a membrane using a measurement of optical properties of the fluid and bacteria using one or more dual wavelength optical sources and a detector which is responsive to a particular source during a particular time interval.

Figure 1:
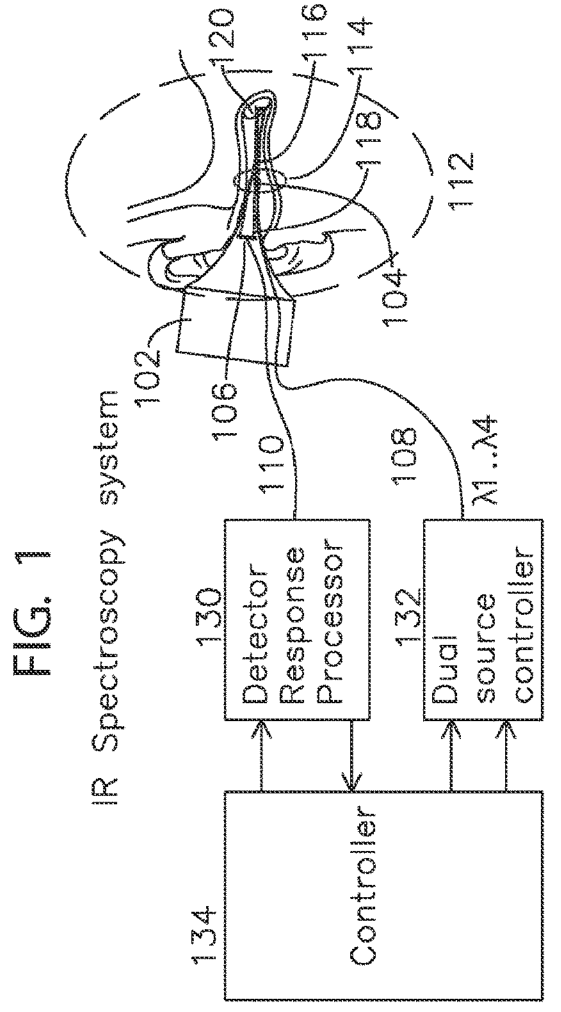
FIG. 1 shows a block diagram of an infrared spectroscopy system for making measurements of a tympanic membrane.
Figure 2:
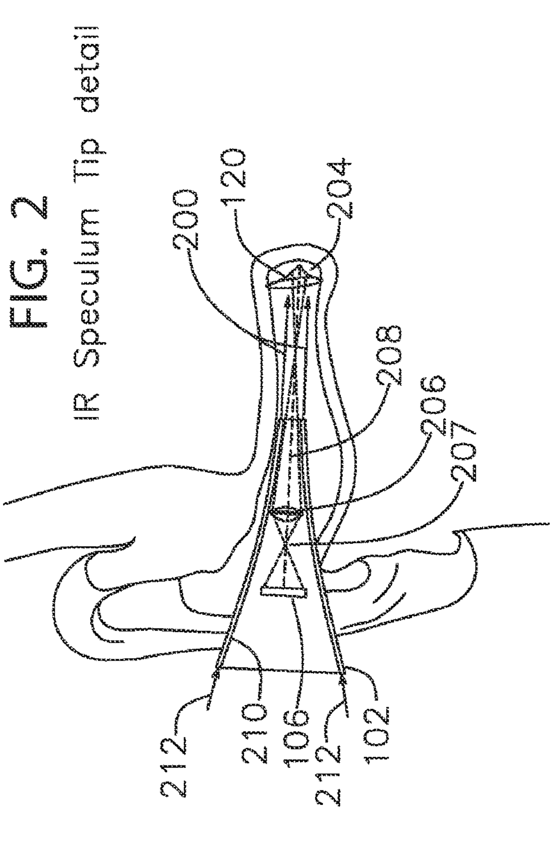
FIG. 2 shows a detail view of a speculum tip and optical components with respect to a tympanic membrane.

FIG. 1 shows a block diagram for an infrared (IR) spectroscopy system with an expanded view of the speculum tip in FIG. 2. A controller 134 is coupled to a detector response processor 130 and dual source controller 132. The dual source controller 132 enables and provides power to a first optical source (not shown) at a first wavelength λ1 and a second wavelength source (not shown) at a second wavelength λ2 during alternating intervals. The optical energy from the sources is directed through a speculum tip 102 and onto the front (distal) surface of a tympanic membrane 120 to be characterized, with the speculum tip 120 minimizing the reflected optical energy from inside the speculum tip 120 to the detector 106 through paths other than those which first reflect from the tympanic membrane 120. The reflected optical energy is sensed by an optical detector 106 and provided to image processor 130, which compares the reflected optical energy at a first wavelength to reflected optical energy at a second wavelength, and forms a metric such as ratio of reflected optical power measured at the detector in each wavelength $$\frac{\lambda 1_{refl}}{\lambda 2_{refl}}.$$

The wavelength metric may be used to estimate the likelihood of presence of bacteria or bacterial load in the inner ear fluid on the opposite (proximal) surface of the tympanic membrane 120.

FIG. 2 shows an example detailed view of IR speculum tip 102 with respect to other elements of an example embodiment. For bacterial measurement, first wavelength 21 and adjacent second wavelength 22 optical energy 212 may be coupled to the speculum tip 102 in any known manner which then couples to an annular light pipe, such as with a plurality of optical fibers positioned around the circumference of speculum tip 102, thereby coupling optical energy 200 to tympanic membrane 120 and to fluid 204 which may be on the proximal side of tympanic membrane 120, but without directly coupling to detector 106 until after reflection from tympanic membrane 120 and any fluid 204 which may lie opposite the tympanic membrane 120 distal surface which is facing the speculum tip 102. It may be additionally advantageous to add structure which exclude optical energy from sources other than tympanic membrane reflection. Reflected optical energy, which includes responses from tympanic membrane 120 and any fluid 204 which may be present, is focused by lens 206 into a dual range wavelength detector 106. In one example embodiment, the inner surfaces of speculum tip 212 are reflective and no lens or focusing mechanism 206 is present to guide unfocused reflected light to detector 106. Where a lens 206 is not present, the detector 106 is responsive to optical energy traveling directly from the tympanic membrane, as well as optical energy which has reflected from the inner reflective surface of the speculum tip 212. In this embodiment, identification of the selection region may be accomplished using a laser pointer (not shown) or other optical viewing system. The laser pointer emitter may optionally be disabled during measurement intervals to avoid contributing unwanted detector response from the laser pointer scattered reflection. A similar set of third and fourth wavelengths may be used to measure water content with adjacent wavelengths in absorption and non-absorption wavelengths. In another example embodiment, lens system 206 is present with the detector 106 having a small extent and comparatively small number of pixels and positioned at focal point 207, or alternatively it may be placed at an image plane as shown in FIG. 2 with a large number of pixels, such as 50×50 or 100×100, or a resolution which is governed by the pixel pitch and available inner diameter of speculum 102 at the image or focal plane.

Figure 3:
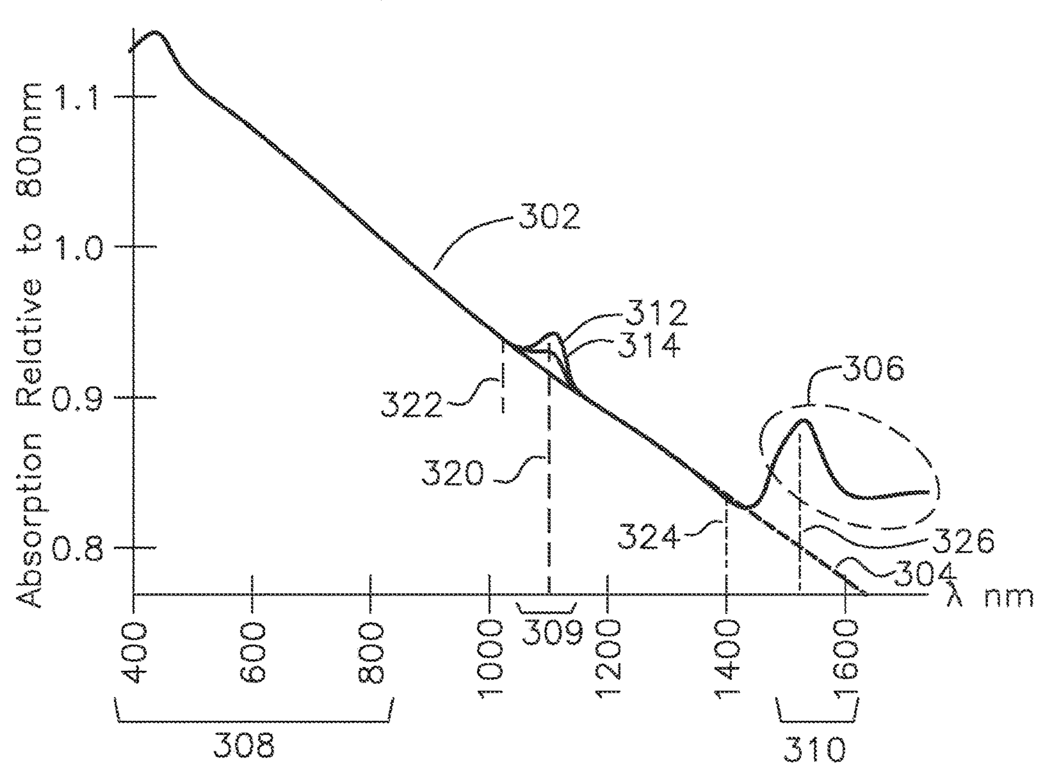
FIG. 3 shows a plot of scattered IR spectral response vs wavelength from a tympanic membrane.

FIG. 3 shows a spectral response for energy reflected from a tympanic membrane with and without bacterial/watery fluid. The reflection characteristic has a characteristic $$\frac{1}{f}$$

absorption falloff associated with Rayleigh scattering, whereby longer wavelengths have fewer scattering interactions and lower absorption than shorter wavelengths. The absorption plot 302 is generally reciprocal with increasing wavelength, however bacteria having a physical length which interacts with optical energy at an associated wavelength, such as the range 309 which has a greater absorption 312,314 for various bacterium in region 309 of the plot for bacterial fluid compared to non-bacterial fluid in response plot 302. Particular bacteria which are absorptive in range 309 include *Haemophilus influenzae, Moraxella catarrhalis*, and *Streptococcus pneumoniae*. Similarly, an elevated absorption peak 306 is found associated with water absorption in a different range of wavelengths. In the present invention, the detector is responsive to reflected optical energy in a first wavelength range 309 such as 1050 nm to 1150 nm which provides for a decreased response at the detector due to bacterial scattering, and the detector uses absorption in an adjacent wavelength 322 such as 1000 nm or the visible optical range 308 of 400 to 800 nm, which may also be used as a fifth wavelength λ5 for pointing and illuminating the region of examination used for forming the λ1 and λ2 or λ3 and 4 metric ratios. In this case, λ5 may be in a visible range or detection wavelength range for a 2D detector 106, with the λ5 source having a narrow dispersion laser (not shown) for illuminating the region of examination and indicating a landmark region such as the "cone of light" of the tympanic membrane for locating the measurement region.

In an illustrative example, FIG. 3 shows a first wavelength 326 with an increased absorption when bacteria is present (region 309) compared to second wavelength 322 which is unaffected by the presence of bacteria, and third wavelength 326 has greater absorption when watery fluid is present compared to fourth wavelength 324 which is adjacent to the absorptive wavelength for watery fluid. These examples are given for illustrative purposes, wavelengths for absorption by bacteria or water may vary from those shown in the example of FIG. 3. In the context of the present specification, wavelength specific absorption may also be referred to as scattering or reflective attenuation. In one example of the invention, a first wavelength operative for increased absorption or scattering in the presence of bacteria is in the range 1050 nm to 1150 nm, and an adjacent wavelength is one below 1050 nm or above 1150 nm. In another example of the invention, a third wavelength operative for increased absorption or scattering in the presence of watery fluid is the range 310 from 1450 nm to 1600 nm, and a fourth wavelength which is adjacent to the third wavelength is below 1450 nm or above 1600 nm.

Figure 4:
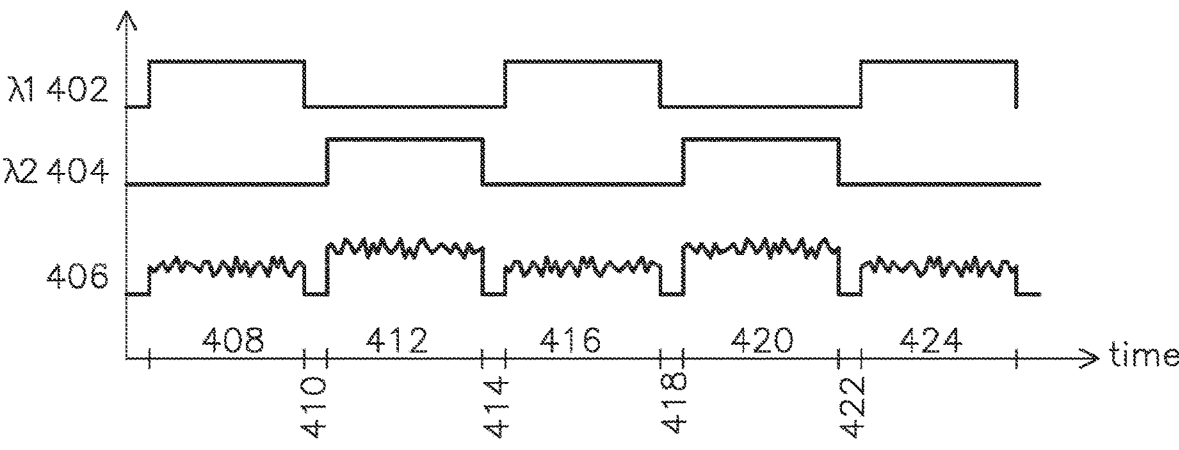
FIG. 4 shows a plot of waveforms for measurement of reflected optical energy from a first and second optical source.

FIG. 4 shows a plot of waveforms for operation of the device of FIGS. 1 and 2, which uses two optical sources such as λ1 and λ2, although the commutation (also known as time multiplexing) for four wavelengths may be done in any order. A first wavelength λ1 optical source 402 is commutated on during intervals 408, 416, and 424 and off during exclusive intervals 412, 420 when the second wavelength λ2 optical source is enabled. Intermediate gaps 410, 414, 418, 422 may be used for ambient light corrections at the detector, which may be used to estimate an ambient light and detector offset value, and thereafter subtracted from the detector response during intervals 408, 416, 424 of λ1, and intervals 412 and 420 of λ2. The detector response 406 includes detector noise, which may be averaged over the measurement interval 408, 416, 424 for the first wavelength λ1, or 412, 420 for the second wavelength λ2. In one example of the invention extended from the one shown in FIG. 4, λ1 is a wavelength of increased bacterial absorption, λ2 is a nearby reference wavelength which is outside the bacterial absorption wavelength of λ1, λ3 is a wavelength for water absorption, λ4 is a wavelength near to λ3 but not affected by water absorption, and λ5 is an optical wavelength for visualization, each wavelength λ1 and 22 are commutated on during exclusive intervals as waveforms 402 and 404 of FIG. 4 for forming a bacterial metric $$\frac{\lambda 1_{refl}}{\lambda 2_{refl}},$$

optionally after which each wavelength λ3 and λ4 are commutated during exclusive intervals 402 and 404 to form fluid metric $$\frac{\lambda 3_{refl}}{\lambda 4_{refl}}.$$

Each corresponding metric may then be compared with a threshold for each metric to arrive at an estimated likelihood of presence of fluid or presence of bacteria. In one example of the invention, the respective bacterial or water fluid detector wavelength responses may be corrected for wavelength-specific attenuation or scattering (in the absence of watery fluid or bacteria) so that each pair of wavelengths (pathogen specific and adjacent) provide a unity metric ratio $$\left(\frac{\lambda 1_{refl}}{\lambda 2_{refl}} \text{ or } \frac{\lambda 3_{refl}}{\lambda 4_{refl}}\right)$$

when bacteria or watery fluid, respectively, are not present.

FIG. 5 shows a block diagram for an optical coherence tomography (OCT) characterization system, which has the benefit of narrow depth of axial specificity, which allows the response being measured to be restricted to a particular axial depth and range of depth, such as the proximal surface of the tympanic membrane and middle ear region. A low coherence source 514 having a plurality of wavelength range outputs includes a first wavelength λ1 and a second wavelength λ2 which are directed along path 518 to first splitter 516, and thereafter to second splitter 526. Half of the optical energy is thereafter directed to the measurement optical path 528, and half to mirror 512 and movable reflector 508, which adjusts the length of the reference path to be equal to the measurement path length which includes the proximal surface of the tympanic membrane and middle ear region. The optical energy returned from the reflector 508 and returned from tympanic membrane 532 combine at second splitter 526, and the summed optical energy continues to first splitter 516 and thereafter to mirror 524 and detector 520. Where the reference optical path (optical distance from splitter 526 to reflector 508) is exactly the same length as measurement optical path (from second splitter 526 to tympanic membrane 532), the coherently summed reference optical energy and reflected optical energy is directed, in sequence, to second splitter 526, first splitter 516, mirror 524, and to detector 520. The short coherence length of source 514 provides depth specificity, which allows measurement of bacterial response, typically with specificity of less than an optical wavelength in depth on the proximal side of tympanic membrane 532. Schematic FIG. 5 is shown for illustration only, other configurations of optical mirrors and splitters may be used.

FIG. 6A shows a first example of a multi-wavelength detector 520A, where a first wavelength λ1 detector 602 is responsive to λ1 and transparent for second wavelength λ2 associated with second detector 604. By bonding a first detector 602 and second detector 604 together using an optically transparent adhesive, the front-facing detector 602 is transparent for the optical energy λ2 of the detector 604 behind it. This construction of the detector 602/604 may require commutation of the various optical sources as was described in FIG. 4, particularly where one of the detectors has an out-of-band response to adjacent wavelength optical energy used for a different measurement, such as water vs bacterial absorption.

FIG. 6B shows another embodiment of a multi-wavelength detector 520A, which utilizes a diffraction grating 608 to separate the various wavelengths λ1, λ2, λ3, λ4, etc. to detector 606 for spatial isolation of each wavelength. Because the various wavelengths are spatially separated, this configuration of detector may permit the four optical sources to be operated continuously and simultaneously, as they are inherently non-interfering because of the spatial separation by wavelength not present in the detector configuration of FIG. 6A. Dark current detector response (the detector response in the absence of optical energy used to establish a baseline response level which is subtracted from a reading when optical energy is present) may be made before or after the optical sources are enabled.

FIGS. 7A, 7B, 7C, 7D, 7E, and 7F show associated waveforms for positional drive 701 and 703, which modulate the axial position of reflector 508 of FIG. 5, where the position "0" corresponds to position 536*b* of FIG. 5, the position "−0.5" indicates position 536*a*, "+0.5" indicates position 536*c*, and "+1.0" indicates position 536*d*.

For the attenuation plot of FIG. 3, and using λ1 at an exemplar maximum viral attenuation wavelength of 1100 nm and λ2 at an exemplar adjacent wavelength 1000 nm, and λ3 at an exemplar water absorption wavelength of 1500 nm and λ4 at an exemplar nearby wavelength of 1400 nm which is outside the water absorption wavelength, it is possible to compare the relative responses of λ1 with λ2, and λ3 with λ4 to determine the three conditions of clinical interest: absence of watery fluid, presence of effusion fluid without bacteria, and presence of effusion fluid with bacteria, as is desired for subjects suffering from ear discomfort. The apparatus and method thereby providing a diagnostic tool for viral vs bacterial infection, as well as determining that no fluid is present proximal to the tympanic membrane.

Figures 7A, 7B, 7C, 7D, 7E, 7F:
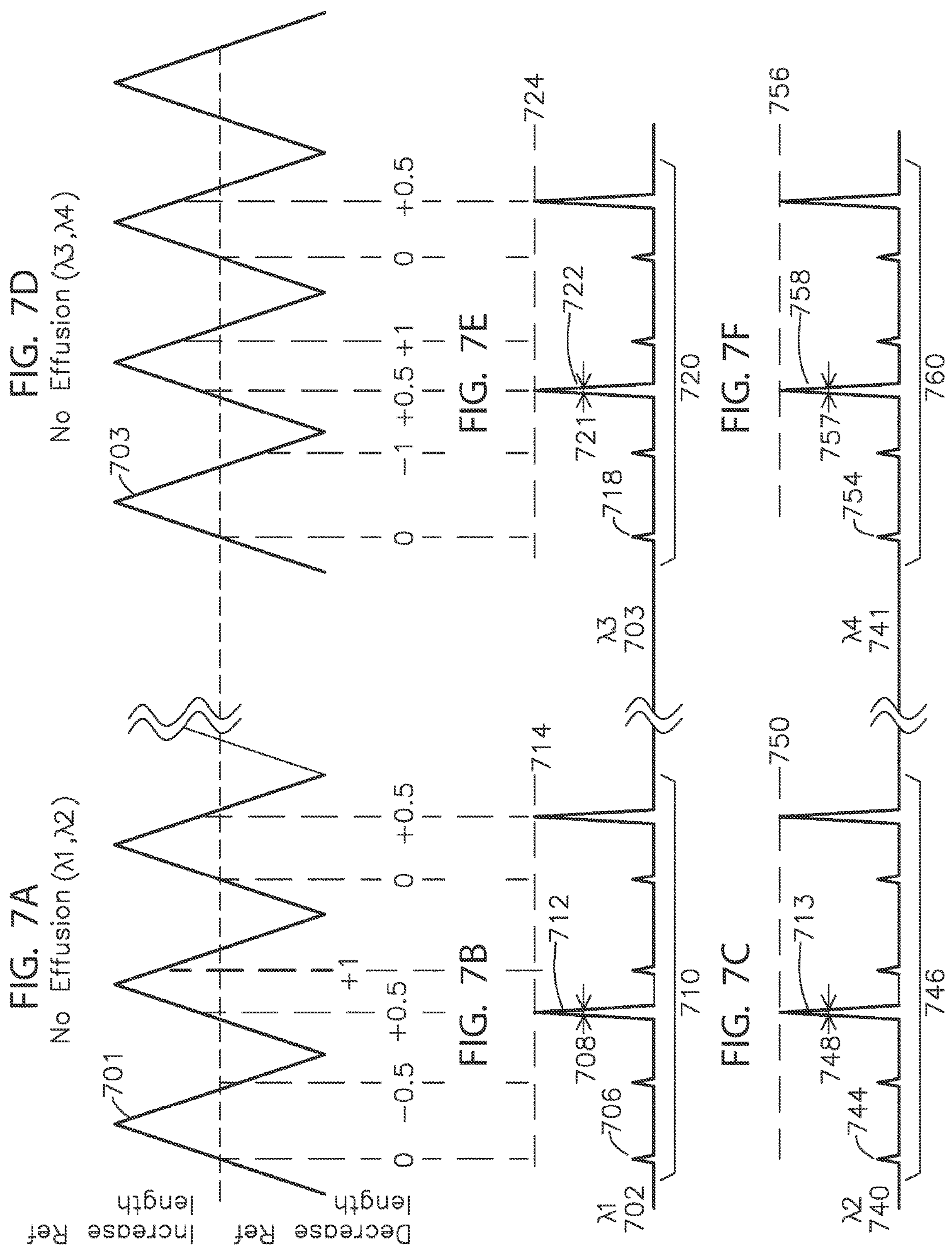
FIG. 7A, FIG. 7B, FIG. 7C, FIG. 7D, FIG. 7E, and FIG. 7F show waveform plots for a normal tympanic membrane.

FIGS. 7A and 7D are plots of axial position for the reflector 508 of FIG. 5, FIGS. 7B and 7C show the λ1 and λ2 responses, respectively, which are differential for bacteria, and FIGS. 7E and 7F show the λ3 and λ4 responses, respectively, which are differential for presence of watery fluid. The waveforms 702, 740, 703, and 741 show equal amplitude detector responses 714 and 750 where no fluid is present proximal to the tympanic membrane. Responses 706, 744, 718, and 754 are minimal coherent reflections due to patches of ear wax, ear follicles, or other minor structures distal to the tympanic membrane, and responses 712, 713, 722, and 758 are the respective detector responses for λ1 through λ4, respectively at the tympanic membrane. The short duration of the responses 708, 748, 721, and 757 at position +0.5 near the tympanic membrane also indicates that only the tympanic membrane is providing return signal, and only over the short duration of coherent reflection from the tympanic membrane. As minimal differential attenuation is present which is specific to wavelength, the response amplitudes 714, 750, 724, and 756 are all equivalent amplitude.

Figures 8A, 8B, 8C, 8D, 8E, 8F:
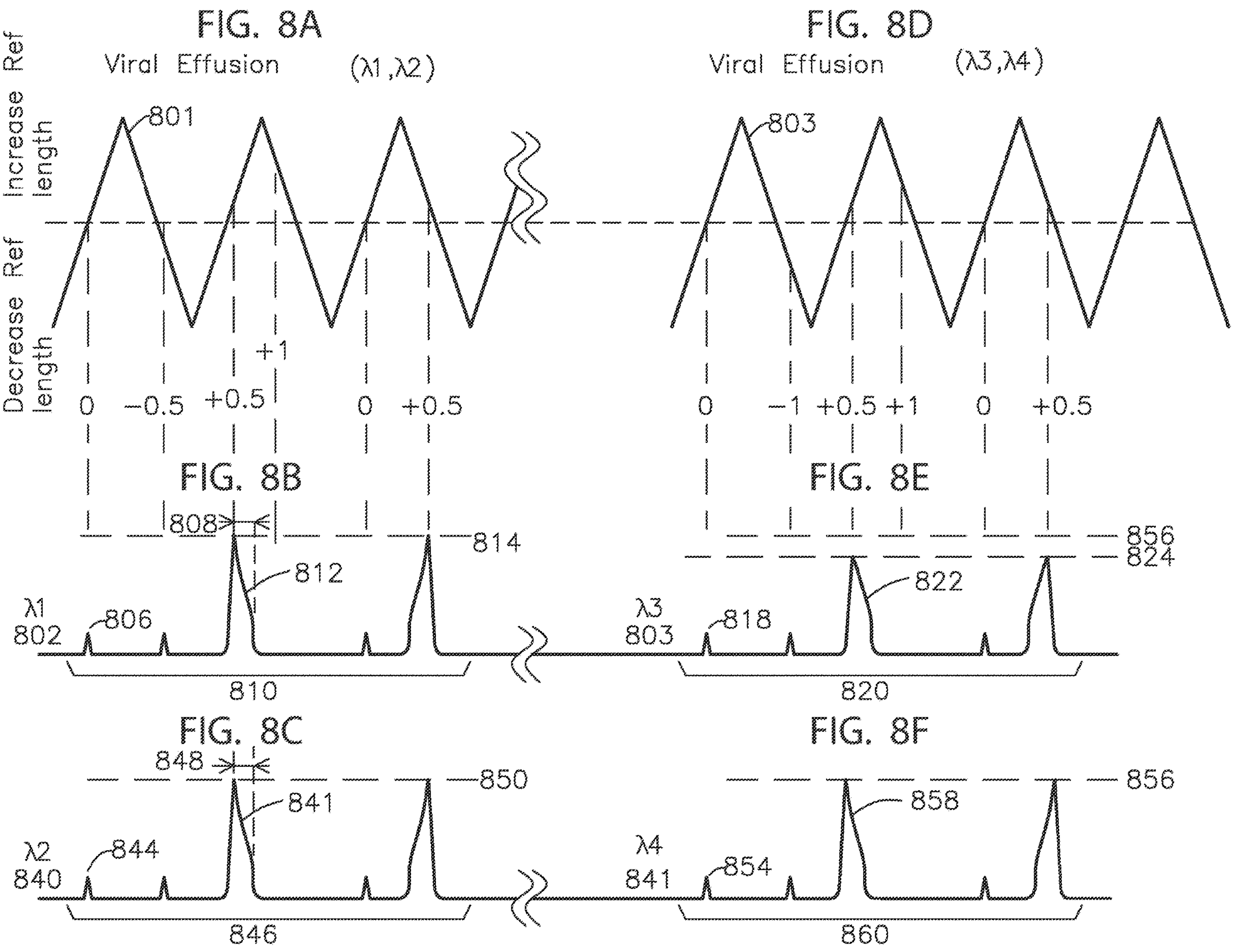
FIG. 8A, FIG. 8B, FIG. 8C, FIG. 8D, FIG. 8E, and FIG. 8F show waveform plots for viral effusion in a tympanic membrane.

FIGS. 8A and 8D similarly show a plot of reflector position 801 and 803, respectively, corresponding to the region of coherence about the tympanic membrane, as was described for FIGS. 7A and 7D. The plots of FIGS. 8B and 8C show the OCT responses from viral (watery) fluid proximal to the tympanic membrane. The responses 806, 844, 818, and 854 distal to the tympanic membrane are minimal, as before. The tympanic membrane responses and proximal responses 812, 841, 822, and 858 have an extended duration of response associated with the fluid boundary proximal to the tympanic membrane, and include a longer time extent 808 and 848 of response, related to the spatially expanded response from fluid adjacent to the tympanic membrane, compared to the narrow tympanic membrane detector response such as 712 of FIG. 7. The peak amplitude detector responses 814 (λ1) and 850 (λ2) are similar in amplitude, whereas the peak response 824 (λ3) is reduced compared to 856 (λ4) because of the differential absorption of water at λ3 compared to λ4.

Figures 9A, 9B, 9C, 9D, 9E, 9F:
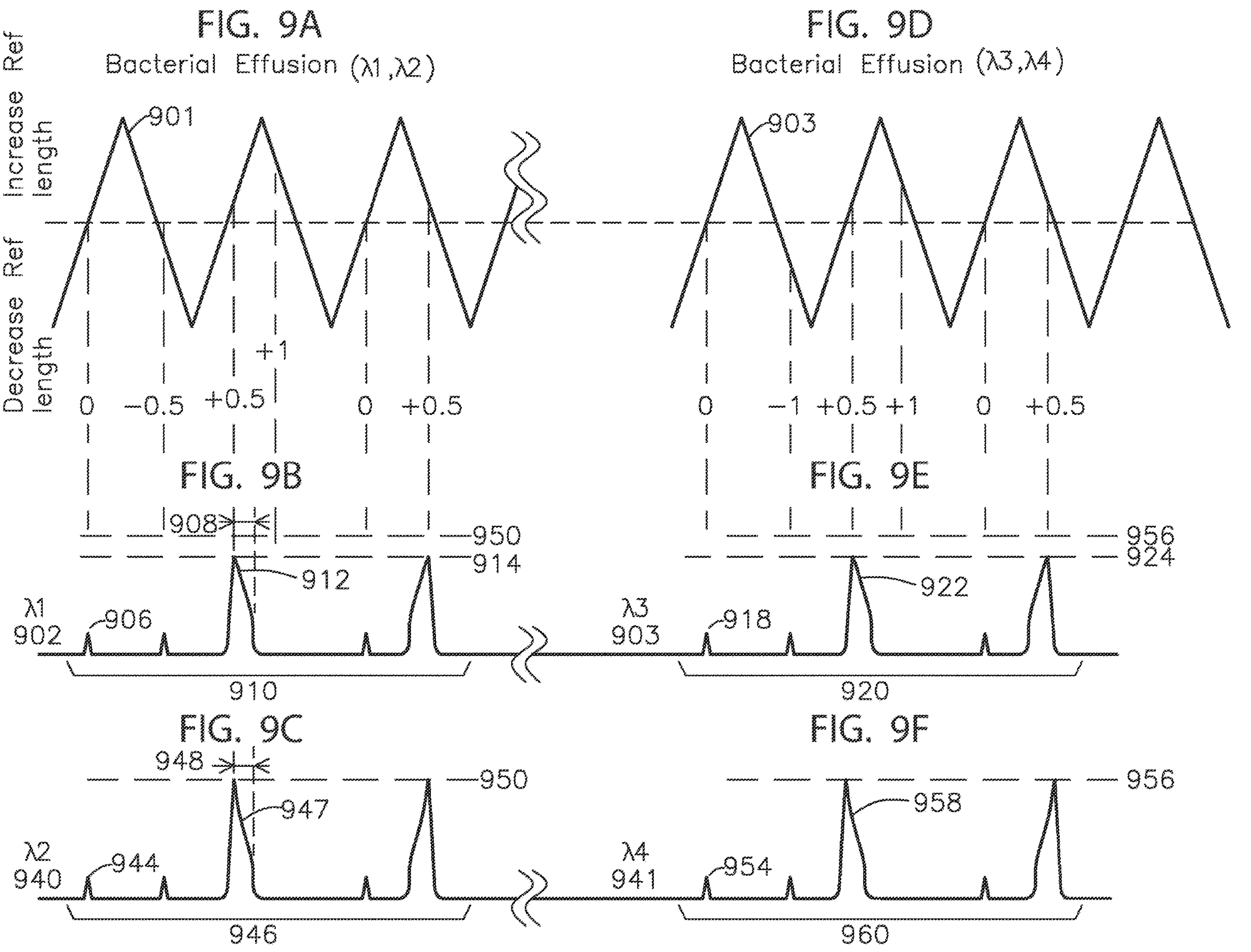
FIG. 9A, FIG. 9B, FIG. 9C, FIG. 9D, FIG. 9E, and FIG. 9F show waveform plots for bacterial effusion in a tympanic membrane.

FIGS. 9A and 9D show the reflector position plots with responses of FIGS. 9B, 9C, 9E, and 9F for bacterial effusion proximal to the tympanic membrane. The amplitude 914 of OCT detector response 912 to λ1 is reduced compared to the detector amplitude response 947 at λ2, which is not as absorptive for bacteria. The extent of OCT response 908 and 948 is lengthened, as before, due to the bacterial concentration which may be adjacent to the tympanic membrane. The water attenuation of λ3 compared to λ4 is shown in plots 903 and 941, with responses 922 attenuated at amplitude 924 compared to plot 958 at greater amplitude 956.

As described in the previous response plots, the ratio of reflected signal λ1/λ2 may be used to estimate bacterial concentration, and the ratio of reflected signal λ3/λ4 may be used to estimate fluid presence adjacent to the tympanic membrane, and the ratio may compensate for lower amplitude response from shorter wavelengths (having more Rayleigh scattering) of each pair of wavelengths such that the ratio is normalized to 1 for the absence of either bacteria or watery fluid in each respective ratio.

Figure 10:
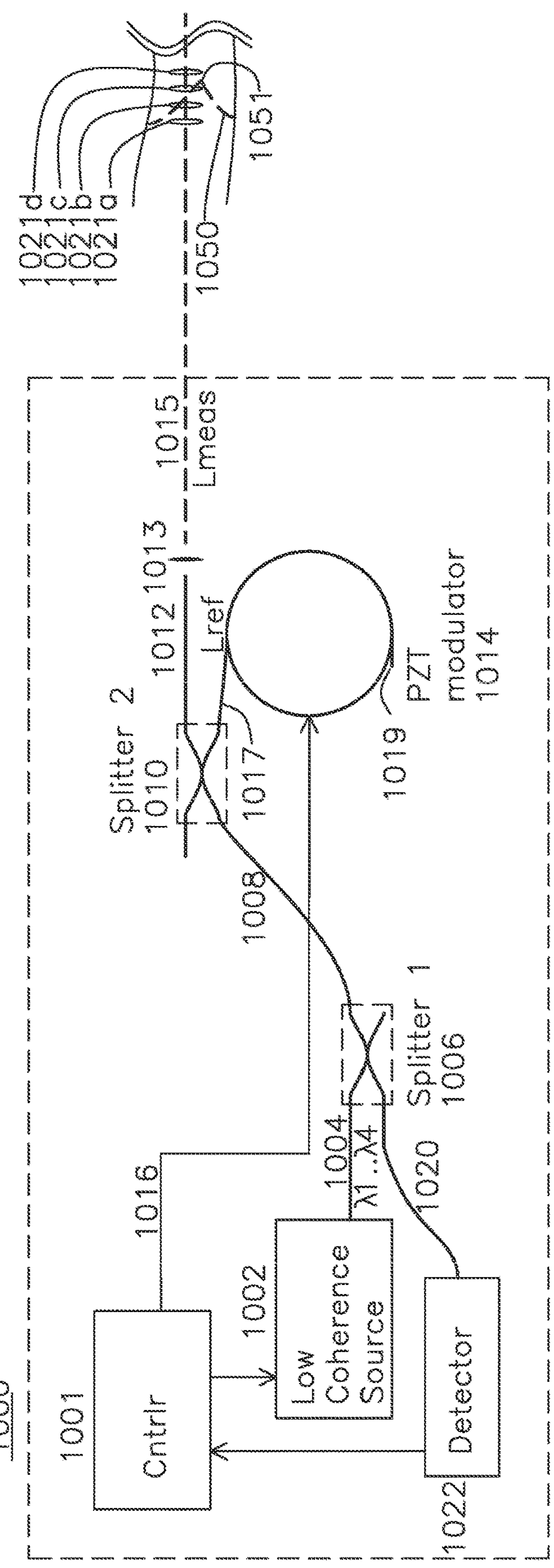
FIG. 10 shows a block diagram of an optical fiber based OCT system for dual wavelength in-fiber dual spectroscopy.

FIG. 10 shows a fiber optic architecture for performing OCT to form a differential measurements previously described. Low coherence source 1002 generates λ1, λ2, λ3, λ4 in a commutated sequence (for detector 1022 of FIG. 6A, or concurrently for the detector of FIG. 6B), which is applied to first splitter 1006, the low coherence source being coupled to optical fiber 1008 and to second splitter 1010, half of the optical source power directed thereafter to optical fiber 1012 and lens 1013, which directs the beam through the speculum tip (not shown), to tympanic membrane 1051, with reflections from the tympanic membrane and adjacent structures directed back along Lmeas path to lens 1013, optical fiber 1012, and back to second splitter 1010. The other half of the power traveling from the source 1002 through splitter 1004 to second splitter 1010 is directed to reference path 1017 with length Lref terminating in a polished fiber end 1019, which reflects optical energy in a counter-propagating direction and back to second splitter 1010. The reference path length Lref is equal to the total measurement length from second splitter 1010 to the tympanic membrane 1050. By adjusting Lref using the PZT modulator 1014 which changes the length of the optical fiber by stretching it longitudinally, the region of optical coherence can be modulated axially about the tympanic membrane.

An optical coherence tomography (OCT) device has a low coherence optical source generating optical energy coupled through a first splitter, thereafter to a second splitter, the second splitter having a measurement optical path to a tympanic membrane and also a reference optical path to a reflector which returns the optical energy to the first splitter, where the reflected optical energy is added to the optical energy reflected from the measurement optical path. The combined reflected optical energy is then provided to the first splitter, which directs the optical energy to a detector. The reflector is spatially modulated in displacement along the axis of the reference optical path such that the detector is presented with an optical intensity and optionally a continuum of optical spectral density from a particular measurement path depth, when the measurement optical path and reference optical path are equal in path length. When the device is positioned with the measurement path directed into an ear canal and directing optical energy to a tympanic membrane, by varying the reference optical path length through translation of the location of the reflector along the axis of the reference optical path, a measurement of optical and spectral characteristics of the tympanic membrane may be performed. Additionally, an external pressure excitation may be applied to provide an impulsive or steady state periodic excitation of the tympanic membrane during the OCT measurement, and a peak response and associated time of the peak response identified. The temporal characteristics and positional displacement of the tympanic membrane can be thereafter examined to determine the tympanic membrane response to the external pressure excitation. The evaluation of the tympanic membrane response from the OCT detector data may subsequently be correlated to a particular viscosity or biofilm characteristic. By examination of the temporal characteristic, an estimate of the viscosity of a fluid adjacent to a tympanic membrane may be determined, and the viscosity subsequently correlated to the likelihood of a treatable bacterial infection.

Figures 11, 12A, 12B:
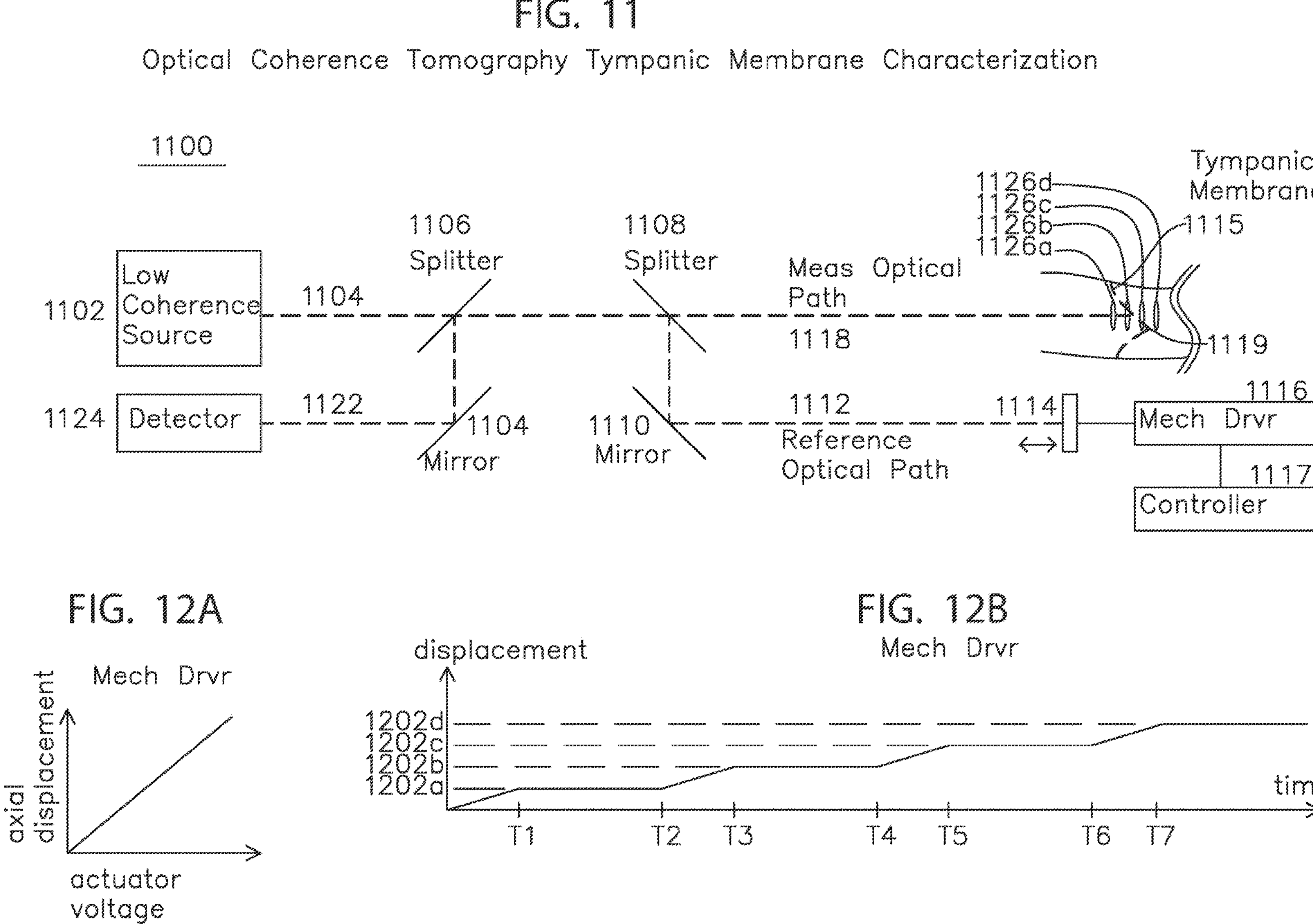
FIG. 11 shows a block diagram of an optical coherence tomography characterization system.
FIG. 12A shows a plot of mechanical actuator displacement vs actuator voltage.
FIG. 12B shows a plot of reference path length over time, as controlled by actuator voltage or current.

FIG. 11 shows a block diagram for an optical coherence tomography (OCT) device 1100 according to one example of the invention. Each reference number which appears in one drawing figure is understood to have the same function when presented in a different drawing figure. A low coherence source 1102 such as a broadband light emitting diode (LED) with a collimated output generates optical energy along path 1104 to first optical splitter 1106, and optical energy continues to second optical splitter 1108, where the optical energy divides into a measurement optical path 1118 and a reference optical path 1112, which include the segment from second splitter 1108 to mirror 1110 to path length modulator 1114. The optical energy in the measurement optical path 1118 interacts with the tympanic membrane 1120, and reflected optical energy counter-propagates to the detector via path 1118, where it is joined by optical energy from reference optical path 1112 reflected from mirror 1110 and splitter 1108, and the combined reflected optical energy propagates to first splitter 1106, thereafter to mirror 1105, and to detector 1124 via path 1122. Detector 1124 generates an electrical signal corresponding to the intensity of detected optical energy on path 1122, which is a steady state maximum when the path length for reflected optical energy from the tympanic membrane is exactly the same length as the reference optical path, and a temporal maximum if the reference optical path length is swept over a range, such as by actuating path length modulator 1114 over time. Each type of reflective membrane will produce a characteristic detector signal. For example, as the reference path length traverses through a thin membrane boundary such as a healthy tympanic membrane, a single peak will result corresponding to the single reflective region of the tympanic membrane. If the reference path length is through a fluidic ear such as one containing low-viscosity infectious effusion, an initial peak of the tympanic membrane reflection will subsequently generate a region of extended reflection with an amplitude that drops from optical attenuation of the reflected signal. If the reference path length traverses through the tympanic membrane with a bacterial infection, a bacterial film may be present on the opposite surface of the tympanic membrane, which may produce a greater axial extent of reflection, followed by a pedestal indicating a high scattering coefficient and corresponding increased attenuation. Additionally, the three types of fluid viscosities behind the tympanic membrane (air vs thin fluid vs thick fluid) will respond differently to pressure excitations generated on the tympanic membrane. Accordingly, is possible to modulate the reference optical path length and optionally the pressure adjacent to the tympanic membrane, and examine the nature of the detector output signal and response to excitation pressure to determine the presence or absence of fluid adjacent to the tympanic membrane, the presence or absence of a biofilm such as bacteria adjacent to the tympanic membrane, and the viscosity of fluid adjacent to the tympanic membrane, all from movement of the tympanic membrane on the measurement optical path as presented at the detector output.

In one example of the present invention, the path length modulator 1114 varies the reference path length by a distance corresponding to the measurement path length from 1126*a*, 1126*b*, 1121*c*, and 1121*d* of FIG. 11, corresponding to a region of movement of a tympanic membrane 1115 to be characterized. As modulator 1114 increases the reference path length, the signal delivered to the detector is closer to region 1126*d* and when modulator 1114 decreases the distance of the reference path length, the region signal delivered to the detector is in region 1126*a*.

FIG. 12A shows an example relationship between actuator voltage or current and axial displacement of path length modulator 1114, which is driven by a mechanical driver circuit 1116, which may be a voice coil driver for a voice coil actuator coupled to mirror 1114, modulating the mirror about the optical axis of 1112. The type of driver and path length modulator 1114 is dependent on the highest frequency of displacement modulation, since the energy to displace path length modulator 1114 is related to the mass of the path length modulator 1114, such as the case of a moving mirror. The mirror and actuator may be micro electrical machined system (MEMS) for lower reflector mass and correspondingly faster mirror response. It may be possible to utilize a variety of other path length modulators without limitation to the use of mirrors.

FIG. 12B shows the controller 1117 generating an actuator voltage in a step-wise manner, with the actuator stopping momentarily at each depth. For example, if increased actuator drive results in a longer reference path length, then from T1 to T2, the actuator voltage may be 1202*a*, corresponding to the displacement position 1126*a* of FIG. 11, and the other voltages 1202*b*, 1202*c*, and 1202*d* may correspond to positions adjacent to the tympanic membrane of 1126*b*, 1126*c*, and 1126*d*, respectively.

Figure 13:
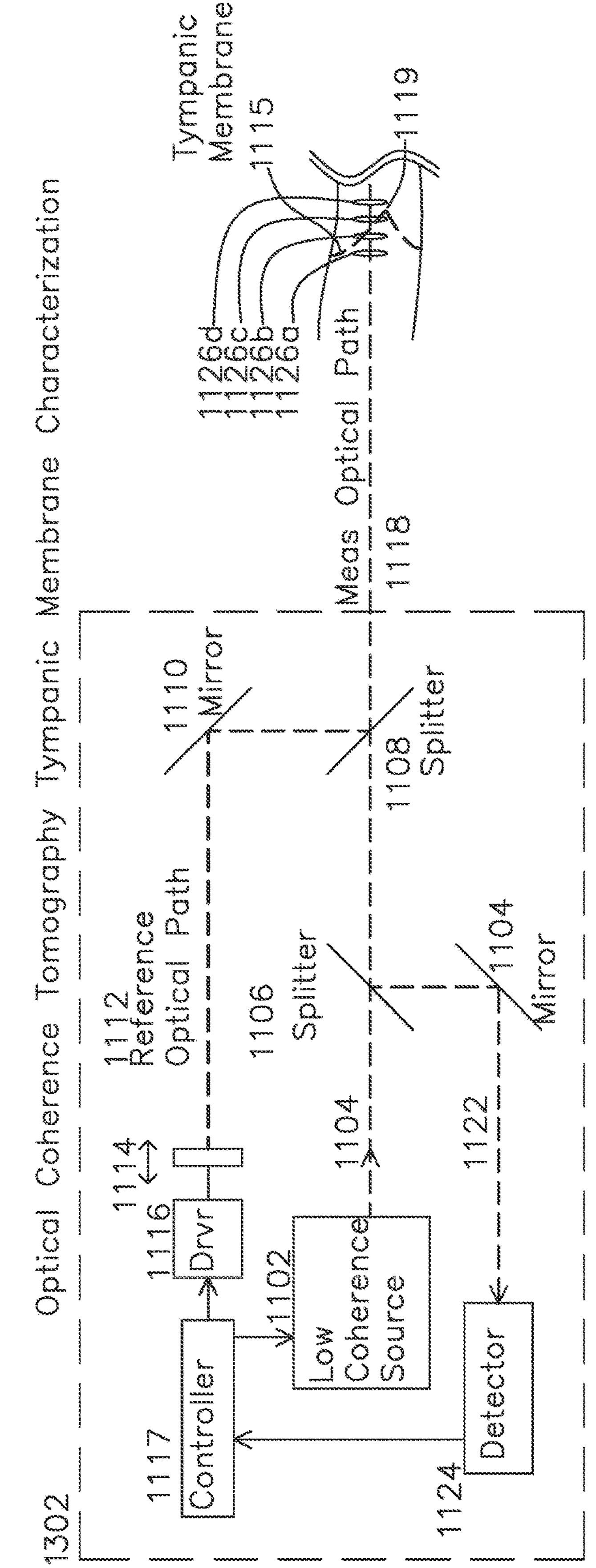
FIG. 13 shows a block diagram for an optical coherence tomography characterization system for use examining a tympanic membrane.

FIG. 13 shows an example OCT tympanic membrane characterization system 302 with the elements arranged to provide a single measurement output. For the case of free-space optics (optical energy which is not confined within a waveguide such as an optical fiber), the system splitters and combiners of FIGS. 11 and 13 are partially reflective mirrors. The principal elements show in FIG. 13 correspond to the same functional elements of FIG. 11. By rearrangement of the reference optical path, the elements of the system may be enclosed, as shown.

Figure 14:
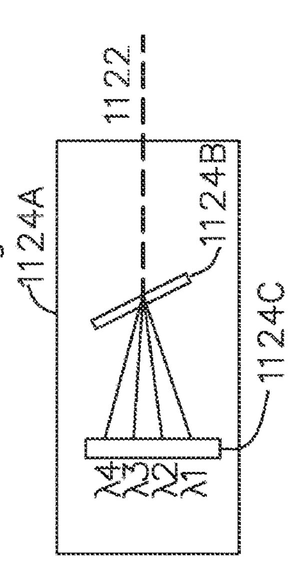
FIG. 14 shows a polychromatic detector.

In one example of the invention, detector 1124 may be a single omni-wavelength optical detector responsive to the total applied optical intensity, and having a characteristic response. In another example of the invention detector 1124 may include a single wavelength filter, or a chromatic splitter and a plurality of detector elements, such that each reflected optical wavelength may be separately detected. FIG. 14 shows collimated optical energy 1122 entering chromatic detector 1124A, where it is split into different wavelengths by refractive prism 1124B, which separates the wavelengths λ1, λ2, λ3, λ4 onto a linear or 2D detector 1124C, which is then able to provide an intensity map for the reflected optical energy by wavelength. Individual detection of wavelengths may be useful where the signature of wavelength absorption is specific to a particular type of bacteria or tympanic membrane pathology. The spectrum of detector response is typically tailored to the reflected optical energy response, which may be in the IR range for an OCT system with more than a few mm of depth measurement capability. In one example of the invention, the detector spectral response for various biological materials is maintained in a memory and compared to the superposition of responses from the plurality of optical detectors. For example, the optical reflective characteristics of cerumen (earwax), a healthy tympanic membrane, an inflamed tympanic membrane (a tympanic membrane which is infused with blood), a bacterial fluid, an effusion fluid, and an adhesive fluid may be maintained in a template memory and compared to the spectral distribution of a measured tympanic membrane response over the axial depth of data acquisition. The detector response at each axial depth over the range of reference optical path length can then be compared to the spectral characteristics of each of the template memory spectral patterns by a controller, with the controller examining the detector responses for each wavelength and the contents of the template memory and estimating the type of material providing the measurement path reflection based on this determination. The detection of a spectral pattern for cerumen may result in the subtraction of a cerumen spectral response from the detector response, and/or it may result in an indication to the user that earwax has been detected in the response, which the user may eliminate by pointing the measurement optical path in a different region of the tympanic membrane.

Because the axial resolution of the optical coherence tomography is fractions of an optical wavelength, it is possible to characterize each of the structures separately on the basis of optical spectrum, even though each of the structures being imaged is only on the order of a hundred microns in axial thickness. The axial resolution of the system may be improved by providing a very narrow optical beam with high spatial energy along the measurement axis and over the axial extent of the tympanic membrane.

Figures 15A, 15B:
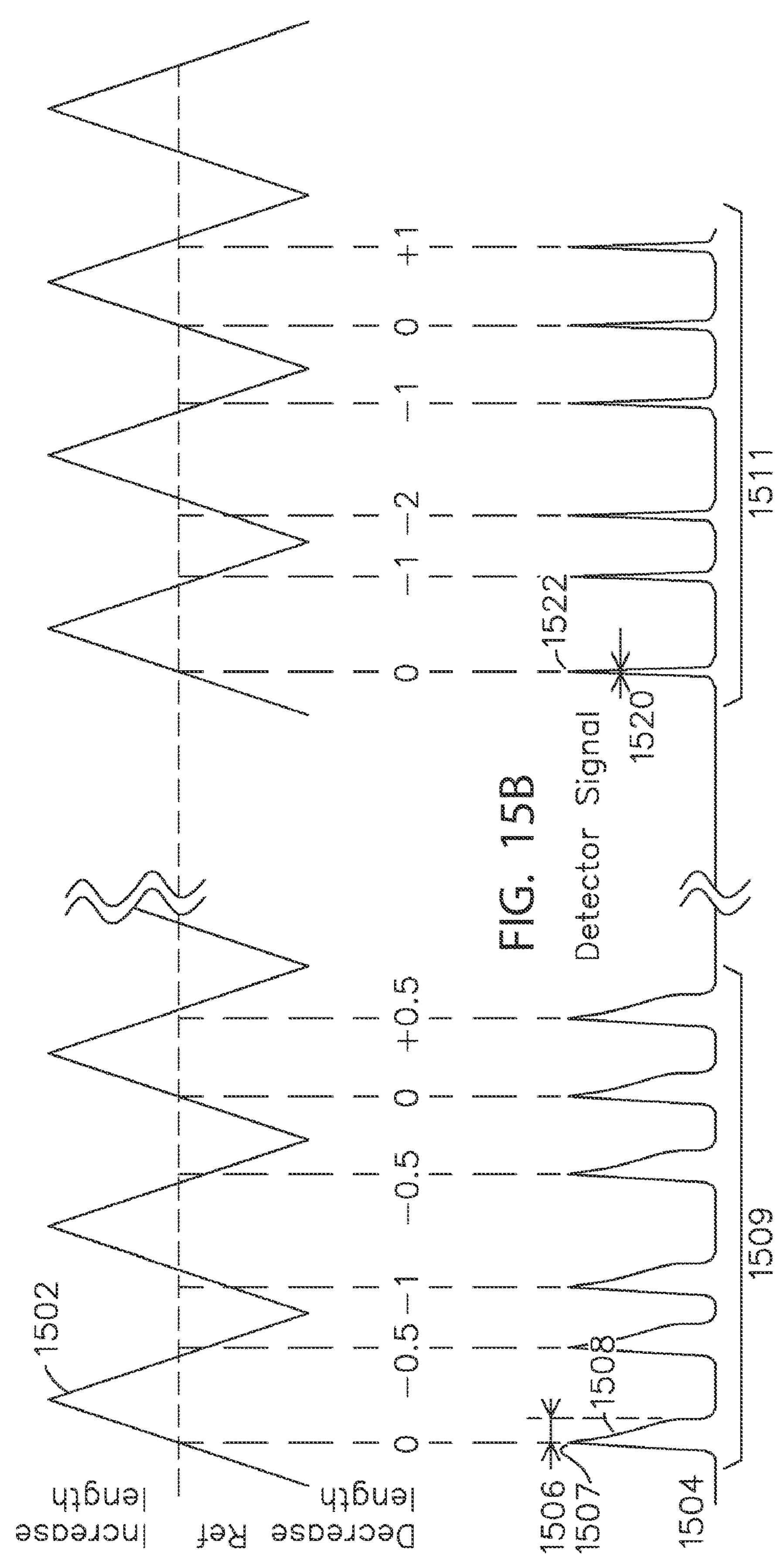
FIG. 15A shows a plot of an example excitation waveform for modulation of a reference length.
FIG. 15B shows a detector signal for a tympanic membrane adjacent to fluid such as from OME and a detector signal for a normal tympanic membrane.

FIGS. 15A and 15B show an example of the invention for use in detecting position of a tympanic membrane over time. The controller 1117 generates a triangle waveform 1502 for use by the path length modulator, which directs the optical energy to the tympanic membrane, which may have fluid adjacent to it, and the fluid may have a particular viscosity, which may be known to increase during the progression of a bacterial infection. Bacterial infections are known to provide a biological film on the surface of a membrane, such as the tympanic membrane, with specific optical reflection characteristics. The optical signal is directed through the outer ear canal towards the tympanic membrane to be characterized, and the detector responses of FIG. 15B are examined by controller 1117 of FIG. 13. A first set of waveforms 1509 shows a time domain response which includes an initial peak 1507 associated with the strong reflection of the sharp reflective optical interface provided by the tympanic membrane at a first reflective interface, and the fluid behind the tympanic membrane also generates a signal which attenuates with depth, shown as a sloped pedestal 1508. The presence of pedestal 1508 indicates the presence of fluid behind the tympanic membrane. This may be contrasted with the second set of responses 1511 for a normal tympanic membrane, such as the peak of waveform 1522, which is comparatively narrow and of shortened duration 1520, as reflective fluid is not present behind the tympanic membrane.

In an additional embodiment of the invention, the tympanic membrane itself may be modulated by an external excitation source, such as an air puff, or a source of air pressure which is modulated over time. Where an external pressure excitation source is provided, and the pressure excitation is selected to provide less than 1% displacement of the tympanic membrane, for example, the relative temporal position of the peak optical signal will indicate the position of the tympanic membrane. Because the refresh rate of the system is optical, rather than acoustic of prior art ultrasound devices, the speed of interrogation of the tympanic membrane is only limited by the rate of modulation of the path length modulator 1114, which may be several orders of magnitude faster than an ultrasound system. Additionally, the axial resolution of an optical system relying on optical interferometry is much greater than the axial resolution of an ultrasound system which is governed by transducer ringdown. Additionally, because the acoustic impedance boundary between air and the tympanic membrane is extremely large, the ultrasound penetration depth of ultrasound to structures beyond the tympanic membrane is very limited. By contrast, the optical index of refraction ratio from air to tympanic membrane is many orders of magnitude lower than the ultrasound index of refraction ratio across this boundary, so the optical energy loss at the interface is lower. The optical penetration is primarily bounded by the scattering losses associated with the tympanic membrane and structures beyond the tympanic membrane interface, and these losses may be mediated in part by using a very high optical energy which is pulsed with a duty cycle modulation to maintain the average power applied to the tympanic membrane in a reasonable average power range.

Figure 16:
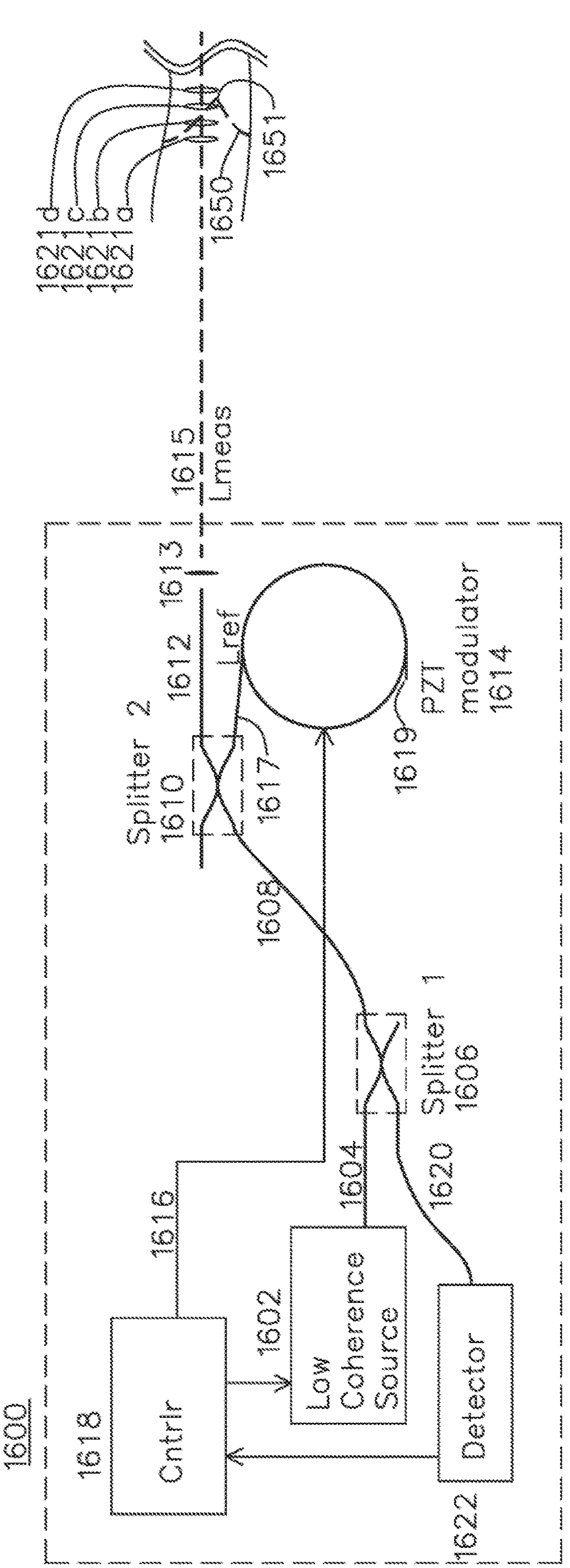
FIG. 16 shows an optical waveguide system for measurement of a tympanic membrane.

FIG. 16 shows a fiber-optic example of an optical coherence tomography system 1600. Controller 1618 coordinates the various subsystems, including enabling low coherence source 1602, which couples optical energy to an optical fiber 1604, which delivers this optical energy thereafter to a first splitter 1606, thereafter to optical fiber 1608 and to second splitter 1610. Optical energy from second splitter 1610 is directed down two paths, one a measurement path 1612 with length Lmeas 1615 to a tympanic membrane, and the other to reference optical path 1617 with length Lref and terminating into an open reflective fiber end 1619, which may alternatively be a mirrored polished end or optical reflective termination, with the optical path 1617 including an optical fiber wrapped around a PZT modulator 1614, which changes dimensional shape and diameter when an excitation voltage is applied to the PZT. When the PZT modulator 1614 is fed with a sine wave or square wave excitation, the PZT modulator 1614 increases and decreases in diameter, thereby providing a variable length Lref. The PZT modulator 1614 is also capable of high speed fiber length modulation in excess of 100 Khz in frequency. Other fiber length modulators known in the art may be used for rapidly changing the length of optical fiber on the Lref path, with the PZT modulator 1614 shown for reference only. The combined optical energy from the Lmeas path and Lref path reach the second splitter 1610 and return on fiber 1608, comprising the sum of optical energy reflected from PZT modulator 1614 and reflected from the tympanic membrane 1650. The combined optical energy travels down path 1608 to first splitter 1606, through fiber 1620, and to detector 1622, where the coherent optical energy superimposes and subtracts, forming a detector 1622 output accordingly, which is fed to the controller 1618 for analysis. The controller 1618 also generates the PZT modulator excitation voltage 1616, such as the voltage or current waveform 1502 of FIG. 5A, and may also generate a signal to enable the low coherence source 1602, and perform analysis of the detector 1622 response, which may be a single intensity value over the wavelength response of the detector 1622, or the individual wavelength output provided by the sensor of FIG. 14. The controller acts on the detector responses in combination with the Lref modulation function to determine an effusion metric which may be correlated to the likelihood of fluid being present adjacent to a tympanic membrane, and also provide an indication of the viscosity of the fluid adjacent to the tympanic membrane.

FIG. 17 shows an extension of FIG. 16 with an external tympanic membrane excitation generator 1704 which delivers miniscule pressure changes such is actuated by a voice coil actuator or other pressure source, preferably with peak pressures below 50 deka-pascals (daPa) for application to a tympanic membrane. The modulation of the reference path length by the PZT modulator 1614 is at a rate which exceeds the highest frequency content of the excitation generator 1704 by at least a factor of 2 to satisfy the Nyquist sampling requirement.

In one example of the invention, the reference path length is modulated by a first modulator and second modulator operative sequentially, where the first modulator provides a large but comparatively slow reference path length change, and the second modulator provides a small but comparatively fast reference path length change. In this manner, the first modulator is capable of placing the region of OCT examination within a region of interest such as centered about a tympanic membrane, and the second modulator is capable of quickly varying the path length to provide a high rate of change of path length (and accordingly, a high sampling rate) for estimation of tympanic membrane movement in response to the pressure excitation.

It can be seen in the tympanic membrane shown as 1115 in FIGS. 11 and 13, and 1650 in FIGS. 16 and 17, that the tympanic membrane has a conical shape with a distant vertex (1119 of FIGS. 11 and 13, 1651 of FIGS. 16 and 17), which is known in otolaryngology as the "cone of light", as it is the only region of the tympanic membrane during a clinical examination which provides a normal surface to the incident optical energy. Similarly, when using an ultrasonic source of prior art systems, the cone of light region is the only part of the tympanic membrane which provides significant reflected signal energy. The optical system of the present invention is operative on the reflected optical energy from the surface, which need not be normal to the incident beam for scattered optical energy, thereby providing another advantage over an ultrasound system.

FIG. 18A shows an example sinusoidal pressure excitation from excitation generator 1704 applied to a tympanic membrane, such as a sinusoidal waveform 1821 applied using a voice coil diaphragm actuator displacing a volume sufficient to modulate a localized region of the tympanic membrane or surface pressure by 100 daPa (dekapascals) p-p. Sub-sonic (below 20 Hz) frequencies may require sealing the localized region around the excitation surface, whereas audio frequencies (in the range 20 Hz to 20 kHz) and super-audio frequencies (above 20 kHz) may be sufficiently propagated as audio waves from generator 1704 without sealing the ear canal leading to the tympanic membrane to be characterized. The sinusoidal pressure excitation 1821 results in a modulation of the surface, which is shown as plot 1832, as the modulation in surface position corresponds to a change in the associated Lref path length by the same amount. Each discrete circle of waveform 1832 represents a sample point from the OCT measurement system 1700, corresponding to the Lref path length and change in tympanic membrane position, with each point 1332 representing one such sample. In one example embodiment of the invention, a series of sinusoidal modulation excitation 1821 frequencies are applied, each with a different period 1822, and the delay in response 1830 and peak change in Lref are used in combination to estimate the ductility or elasticity of the tympanic membrane, fluid viscosity, or other tympanic membrane or fluid property. In the present examples, there is a 1:1 relationship between the displacement of the tympanic membrane and associated change in path length of the reference path which results in the peak response. For example, if the scale of FIG. 15B is a sequence of 0, −0.5 mm, −1 mm, −0.5 mm, 0 mm, 0.5 mm, etc, then this represents a corresponding displacement in the tympanic membrane by these same distances. By applying a series of audio and sub-audio tones with various cycle times 1822 and measuring the change in Lref as shown in plot 1832, it is possible to estimate the displacement of the tympanic membrane and extract frequency dependent characteristics such as viscosity or elasticity of the fluid behind the tympanic membrane. For example, an exemplar elasticity metric measurement associated with the changed density or viscosity of the fluid could be an associated change in surface or membrane response time 1874 for a step change, or phase delay 1830 for a sinusoidal frequency. In this manner, a frequency domain response of the surface may be made using a series of excitations 1821 and measuring a series of surface responses 1832. The reference path modulator 1614 of FIGS. 16 and 17, or mirror 1114 of FIG. 13, may include a first path length modulator which centers the reference path length to include the tympanic membrane, and a second path length modulator which rapidly varies the reference path length to provide adequate sampling of the axial movement of the tympanic membrane.

Whereas FIG. 18A shows a sinusoidal excitation which may be provided in a series of such excitations to generate a phase vs. frequency response plot of the surface displacement from the series of measurements, FIG. 18B shows a time domain step response equivalent of FIG. 18A, where a surface step pressure excitation 862 of 50 daPa peak is applied to the tympanic membrane, which generates the measured tympanic membrane displacement sequence 1872. It is similarly possible to characterize the surface response based on a time delay 1874 and amplitude response (shown as 0.5 mm) for displacement response plot 1872.

In one example of the invention, a separate low-coherence optical source 1102 or 1602 such as an infrared range source is used for increased penetration depth, and a separate visible source (not shown) is used co-axially to indicate the region of the tympanic membrane being characterized while pointing the measurement optical path onto the tympanic membrane. The optical source 1102 or 1602 may be an infrared sources to reduce scattering, thereby providing additional depth of penetration. In another example of the invention, the low-coherence optical source 1102 or 1602 is a visible optical source, thereby providing both illumination of the tympanic membrane region of interest, and also measurement of displacement of the tympanic membrane, as previously described.

The present examples are provided for understanding the invention, it is understood that the invention may be practiced in a variety of different ways and using different types of waveguides for propagating optical energy, as well as different optical sources, optical detectors, and methods of modulating the reference path length Lref. The scope of the invention is described by the claims which follow.

The foregoing is a description of preferred embodiments of the invention. It is understood that various substitutions can be made without limitation to the scope of the invention. For example, other wavelengths may be preferable for bacterial absorption or water absorption than those specified.

What is claimed is:

1. A method for diagnosing otitis media of a patient, the method comprising:

(a) directing a first optical energy along a measurement path, wherein the measurement path crosses a tympanic membrane and the first optical energy interacts with one or more of the tympanic membrane or a fluid adjacent the tympanic membrane;

(b) directing a second optical energy along a reference path;

(c) combining the first optical energy and the second optical energy at a detector after the first optical energy has interacted with the one or more of the tympanic membrane or the fluid adjacent the tympanic membrane and the first and second optical energies have traversed the measurement and reference paths, respectively, the combined first and second optical energies generating a detector response at the detector;

(d) comparing the detector response with a first contents of a template memory corresponding to an effusion fluid with a bacterial effusion, and comparing the detector response with a second contents of the template memory corresponding to the effusion fluid with a viral effusion, wherein the template memory stores one or more characteristics for a type of the effusion fluid; and (e) characterizing the type of the effusion fluid, wherein the characterizing comprises distinguishing the type of the effusion fluid between the effusion fluid with the bacterial effusion and the effusion fluid with the viral effusion based on the one or more characteristics.

2. The method of claim 1, wherein the detector response comprises a wavelength dependent response.

3. The method of claim 2, further comprising comparing the wavelength dependent response to a template response of at least one known material, the template response being stored in the template memory.

4. The method of claim 3, wherein the template response comprises a template response of at least one of cerumen, healthy tympanic membrane, inflamed tympanic membrane, bacterial fluid, effusive fluid, or adhesive fluid.

5. The method of claim 1, further comprising indicating a presence of at least one of cerumen, healthy tympanic membrane, inflamed tympanic membrane, bacterial fluid, effusive fluid, or adhesive fluid to a user.

6. The method of claim 1, wherein the type of the effusion fluid comprises stored characteristics for a bacterial ear infection and a viral ear infection.

7. The method of claim 1, further comprising, before (a), directing a non-contact force through an air medium to one or more of a tympanic membrane or a fluid adjacent the tympanic membrane.

8. The method of claim 7, wherein the characterizing comprises determining a membrane metric from the detector response in response to the non-contact force.

9. The method of claim 8, wherein the membrane metric comprises at least one of an elasticity or a viscosity of the tympanic membrane or the fluid adjacent the tympanic membrane.

10. The method of claim 9, wherein the membrane metric is based on at least one of: a width of the detector response, a pedestal width of the detector response, or a reflected wavelength profile of the detector response.

11. The method of claim 9, wherein the non-contact force comprises an air puff or a pressure excitation.

12. The method of claim 7, wherein the non-contact force comprises an impulsive excitation.

13. The method of claim 7, wherein the non-contact force comprises a periodic excitation.

14. The method of claim 13, wherein a frequency of the periodic excitation is within a range from 20 Hz to 20 kHz.

15. A system for diagnosing otitis media of a patient, the system comprising:

an interferometer configured to direct light energy along a reference path and a measurement path, wherein the measurement path comprises a tympanic membrane; and a controller; and a memory comprising a template memory storing one or more characteristics for a type of an effusion fluid, and wherein the memory is coupled to the controller and stores instructions for the controller to:

receive a detector signal from the interferometer, compare the detector signal with a first contents of the template memory corresponding to the effusion fluid with a bacterial effusion, and compare the detector signal with a second contents of the template memory corresponding to the effusion fluid with a viral effusion, and characterize the type of the effusion fluid, wherein the characterizing comprises distinguishing the type of the effusion fluid between the effusion fluid with the bacterial effusion and the effusion fluid with the viral effusion based on the one or more characteristics.

16. The system of claim 15, wherein the memory further stores instructions for the controller to determine a membrane metric in response to a non-contact force, and wherein the type of the effusion fluid is distinguished between one of the bacterial effusion and the viral effusion based on the membrane metric.

17. The system of claim 16, wherein the membrane metric comprises at least one of an elasticity or a viscosity of the tympanic membrane or a fluid adjacent the tympanic membrane.

18. The system of claim 16, wherein the membrane metric is based on at least one of: a detector response width, a pedestal width, or a reflected wavelength profile.

19. The system of claim 15, further comprising, an excitation generator configured to generate a non-contact force to be directed through an air medium to one or more of the tympanic membrane or the fluid adjacent the tympanic membrane.

20. The system of claim 19, wherein the non-contact force comprises an air puff or a pressure excitation.

21. The system of claim 19, wherein the interferometer comprises a light source.

22. The system of claim 21, wherein the light source comprises a light emitting diode.

23. The system of claim 15, wherein the interferometer comprises a broadband detector.

24. The system of claim 23, wherein the broadband detector is configured to generate a plurality of outputs, each output responsive to a unique range of wavelengths.

25. The system of claim 15, wherein the interferometer comprises a first splitter, which divides the light energy into the reference path and the measurement path, and a second splitter, which combines the reference path and the measurement path.

26. The system of claim 25, wherein the first splitter and second splitter comprise partially reflective mirrors.

27. The system of claim 25, wherein the first splitter and second splitter comprise optical fibers.

28. The system of claim 15, wherein a length of the reference path or a length of the measurement path is modulated using a voltage or current controlled actuator coupled to a mirror.

29. The system of claim 15, wherein a length of the reference path or a length of the measurement path is modulated using a PZT actuator coupled to an optical fiber.

30. The system of claim 15, wherein the template memory stores a template response of one of a plurality of known biological materials.

31. The system of claim 30, wherein the template response comprises one or more characteristics for at least one of cerumen, healthy tympanic membrane, inflamed tympanic membrane, bacterial fluid, effusive fluid, or adhesive fluid.

32. The system of claim 14, wherein the type of the effusion fluid comprises stored characteristics for a bacterial ear infection and a viral ear infection.

* * * * *